(12) United States Patent
Zhang et al.

(10) Patent No.: US 8,112,230 B2
(45) Date of Patent: Feb. 7, 2012

(54) METHOD OF NETWORK-BASED IDENTIFICATION OF MULTICOMPONENT SYNERGY AND COMPOSITIONS FOR USE AS EFFECTIVE COMPONENT OF ANTI-ANGIOGENESIS MEDICINES

(75) Inventors: Ningbo Zhang, Beijing (CN); Shao Li, Beijing (CN); Bo Zhang, Beijing (CN)

(73) Assignee: Tsinghua University

( * ) Notice: Subject to any disclaimer, the term of this patent is extended or adjusted under 35 U.S.C. 154(b) by 223 days.

(21) Appl. No.: 12/436,844

(22) Filed: May 7, 2009

(65) Prior Publication Data

US 2010/0144777 A1    Jun. 10, 2010

(30) Foreign Application Priority Data

Dec. 8, 2008  (CN) .......................... 2008 1 0239284
Dec. 8, 2008  (CN) .......................... 2008 1 0239285
Dec. 8, 2008  (CN) .......................... 2008 1 0239286

(51) Int. Cl.
*G01N 33/48* (2006.01)
*G01N 31/00* (2006.01)
*C12Q 3/00* (2006.01)

(52) U.S. Cl. ................... 702/19; 702/22; 702/23; 435/3

(58) Field of Classification Search ........................ None
See application file for complete search history.

(56) References Cited

OTHER PUBLICATIONS

Scappaticci et al. Combination angiostatis and endostatis gene transfer induces synergistic antiangiogenic activity in vitro and antitumor efficacy in leukemia and solid tumors in mice. Molecular Therapy, 2001, vol. 3, pp. 186-196.*

Lu et al. Application of mixture designs for detection and characterization of multi-drug synergism. First International Conference on Bioinformatics and Biomedical Engineering (ICBBE) published by IEEE, Oct. 29, 2007, pp. 409-413.*

Shao Li, Lijiang Wu and Zhongqi Zhang, "Constructing biological networks through combined literature mining and microarray analysis: a LMMA approach", Bioinformatics 2006,22:2143-2150.

* cited by examiner

*Primary Examiner* — Russell S Negin
(74) *Attorney, Agent, or Firm* — Jennifer Meredith, Esq.; Meredith & Keyhani, PLLC (57) ABSTRACT

A method for determining synergistic effect of a medicine combination including two medicines relating to a disease on the basis of a gene network and medicine-effective genes of each and/or any of said two medicines, comprising: determining a synergy factor ($ST_{1,2}$) of two medicines on the basis of distribution of medicine-effective genes of two medicines; determining a medicine similarity factor ($AS_{1,2}$) of two medicines on the basis of similarity between a set of symptoms which two medicines relates to; and, determining synergistic effect of two medicines according to a product of the synergy factor and similarity factor. Proposed is constructing a disease-related gene network, mapping medicine-effective genes onto the network, and determining the synergistic effect of medicines on the basis of the genes. The present invention also relates to medicine composition of sinomenine and honokiol and of sinomenine and luteolin, each with anti-angiogenesis effect and having good synergistic effect.

9 Claims, 2 Drawing Sheets

METHOD OF NETWORK-BASED IDENTIFICATION OF MULTICOMPONENT SYNERGY AND COMPOSITIONS FOR USE AS EFFECTIVE COMPONENT OF ANTI-ANGIOGENESIS MEDICINES

REFERENCE TO RELATED APPLICATIONS

This application claims foreign priority benefits from Chinese Patent Application No. 200810239284.4, Chinese Patent Application No. 200810239285.9, and Chinese Patent Application No. 200810239286.3, all filed on Dec. 8, 2008.

FIELD OF THE INVENTION

The present invention relates to a method of network-based identification of multicomponent synergy. Also, the present invention relates to a medicine composition having anti-angiogenesis synergistic effect composed of sinomenine and honokiol. Further, the present invention relates to a medicine composition having anti-angiogenesis synergistic effect composed of sinomenine and luteolin.

BACKGROUND OF THE INVENTION

Currently, it is a new approach of disease treatment to develop medicine composition having synergistic effect. By "synergistic effect" we mean the phenomenon that the effect of two medicine components administrated together is greater than the sum of the effects of the two components administrated respectively. In allowed Chinese Patent Application CN200610114226.X (corresponding to U.S. patent application Ser. No. 11/975,320, US-2008-0108642-A1), which was filed by the assignee of the present application and which is incorporated in full text herewith by reference, a medicine composition having synergistic effect was disclosed. However, in the field of medicine development, determination of extent of synergistic effect between medicine components is basically achieved by experiments in vivo and/or in vitro; due to the huge number of possible combinations and complexity of experiment process, high cost and long time are needed for such experiments.

SUMMARY OF THE PRESENT INVENTION

The present inventors developed a network-based method for identifying multicomponent synergy. Also, the present inventors determined that a medicine composition composed of sinomenine and honokiol as an anti-angiogenesis effective component had good synergistic effect. Further, the present inventors determined that a medicine composition composed of sinomenine and luteolin as an anti-angiogenesis effective component had good synergistic effect.

According to an aspect of the present invention, an approach has been provided for quantitively determining extent of synergy of medicines on a given disease by mapping genes and/or gene products, each of which corresponds to at least one of the medicines and is effective on the given disease, onto a gene network. Such an approach features in that the time spent is short, that the cost is low, and that the result is relatively accurate, etc.

According to an embodiment of the present invention, a method has been provided for determining synergistic effect of a medicine combination including two medicines relating to a disease on the basis of a gene network and/or medicine-effective genes of each and/or any of said two medicines, comprising:

determining a synergy factor ($ST_{1,2}$) of said two medicines on the basis of distribution of medicine-effective genes of said two medicines in said gene network;

determining a medicine similarity factor ($AS_{1,2}$) of said two medicines on the basis of similarity between set of symptoms which one of said two medicines relates to and set of symptoms which another of said two medicines relates to; and determining extent of synergistic effect of said two medicines according to a product of said synergy factor and said similarity factor.

According to a further embodiment of the present invention, a method of the present invention for determining extent of synergy of medicines further comprising constructing a disease-related gene network.

In an aspect of the present invention, extent of synergy of two medicines on a given disease are quantitively determined by mapping genes and/or gene products, of each of the two medinces, effective on the given disease onto a gene network and determining the extent of synergy in the context of the gene network.

The effectiveness of the present invention includes:
1) the present invention can be realized on any computer operating Perl; and,
2) the present invention provides an effective approach for pre-experiment determination of extent of synergy of medicine combinations.

In a further aspect, the present invention provides a medicine composition having anti-angiogenesis synergistic effect composed of sinomenine and honokiol.

In a still further aspect, the present invention provides a medicine composition having anti-angiogenesis synergistic effect composed of sinomenine and luteolin.

BRIEF DESCRIPTION OF THE DRAWINGS

FIGS. 1a-1f show experiment data of each of five pairs of medicines of sinomenine and matrine (SM), sinomenine and honokiol (SH), sinomenine and luteolin (SL), sinomenine and quercetin (SQ), sinomenine and paeoniflorin (SP); and FIG. 1e shows scores of maximum suppression rate (MIIR) indicating extent of synergy.

DESCRIPTION OF EMBODIMENTS

The present invention will be described below with reference to its embodiments in a way of illustration rather than limitation.

A method of network-based identification of multicomponent synergy according to an embodiment of the present invention is based on two reasonable principles:

for two medicines having synergy effect to a given disease, their relevant genes should not be separated too far away from one another in gene network, or the interaction between the two medicines would be too weak to produce any significant synergy effect; and the effectiveness of a medicine should be closely associated to the importance of its relevant genes in gene network; the more important the effective gene of a medicine in gene network, the more remarkable the effect of the medicine. Importance of a gene can be measured by the centerness of its corresponding node in gene network.

Based on the two principles, a synergy factor $ST_{1,2}$ reflecting cooperative effect of a medicine combination can be determined in the context of network topology.

According to an embodiment of the present invention, synergy factor $ST_{1,2}$ of a medicine combination is determined as:

$$ST_{1,2} = \frac{1}{2} \times \left( \frac{\sum_i IP_1(i) \times \exp(-\min(d_{i,j}))}{\sum_i IP_1(i)} + \frac{\sum_j IP_2(j) \times \exp(-\min(d_{j,i}))}{\sum_j IP_2(j)} \right)$$ Formula (1)

where:

$IP_1(i)$ and $IP_1(j)$ are factors of node importance of network nodes i and j respectively. According to an embodiment of the present invention, factor of node importance IP of a node is determined by using principal components analysis (PCA) to synthesize a NodeRank centerness, a Betweenness centerness, and/or a Closeness centerness of the node. Detail description of use of principal components analysis (PCA), NodeRank centerness, Betweenness centerness, Closeness centerness and their determination will be given later in the present specification;

$d_{i,j}$ is the shortest network distance/path from node i to node j, and $d_{j,i}$ is the shortest network distance/path from node i to node i. Calculation of the shortest network distance will be explained later in the present specification.

A method of network-based identification of multicomponent synergy according to an embodiment of the present invention is further based on medicine similarity in addition to disease-related gene network topological information. According to an embodiment of the present invention, medicine similarity is indicated by a similarity coefficient ($AS_{1,2}$), by which the synergy factor ($ST_{1,2}$) is weighted. A basic idea of medicine similarity is that the greater the similarity between diseases treated by two medicines, the greater the possibility that the two medicines have synergy effect when they are used to treat a relevant disease. The relation of correspondance of a medicine and relevant diseases can be retrieved, on the basis of genes, from data in OMIM (Online Mendelian Inheritance in Man, www.ncbi.nlm.nih.gov/omim). Specifically, as long as one gene among the genes corresponding to a medicine is within a set of genes that lead to a disease, we will determine that a relation of correspondance exists between this medicine and this disease. In this way, a first medicine corresponds to a first group of diseases, and a second medicine corresponds to a second group of diseases, and we obtain $$AS_{1,2} = \frac{\sum_{i,j} P_{i,j}}{N},$$

where $P_{i,j}$ is the similarity factor between diease i in the first group of diseases and disease j in the second group of diseases, and N is for all pairs of diseases between the the first and second groups of diseases.

A method for determining $P_{i,j}$ was provided by Van Driel, M. A., et al. in "A Text-Mining Analysis of the Human Phenome", Eur. J. Hum. Genet. 2006, 14, 535-542, which included mapping each syndrome item in OMIM database to a set of (0,1) vectors in accordance with standard vocabulary. Thus, two given syndromes, in accordance with their description in words in OMIM database, can be mapped to two sets of (0,1) vectors $\overline{v1}$ and $\overline{v2}$ of standard vocabulary. Then, the $P_{i,j}$ value is determined as the cosine value cos θ of the angle between the two vectors $$\cos\theta = \frac{\overline{v1} \cdot \overline{v2}}{|\overline{v1}||\overline{v2}|}.$$

Using this method, the present inventors had determined a $AS_{1,2}$ value of 0.17075 for sinomenine and matrine, a $AS_{1,2}$ value of 0.15897 for sinomenine and honokiol, and a $AS_{1,2}$ value of 0.17050 for sinomenine and luteolin.

From the above, a formula for synergistic effect scoring of a method of network-based identification of multicomponent synergy according to the present invention is:

$$S_{1,2} = ST_{1,2} \times AS_{1,2}$$

Collection of medicine-effective genes and/or gene products can be carried out prior to performing the network-based identification method for multicomponent synergy of the present invention, as a preparative work for applying a method according to the present invention, which can include reading of references on medicines and collection of information of genes and/or gene products that contribute to the medicine effect concerned. Said references are available from such as PubMed (http://www.ncbi.nlm.nih.gov/sites/entrez?db=PubMed) and/or CNKI (http://www.cnki.net/).

Then, a disease-related gene network needs to be determined, such as by anyone of the following approaches:

1) using LMMA-BioNet Biological Network Construction Software developed by the present inventors (Shao L I, Ningbo ZHANG, and Lijiang W U, LMMA-BioNet Biological Network Construction Software, Computer Software Copyright No. 2008SRBJ0202; Reference: Li S, Wu L J, Zhang Z Q. Constructing biological networks through combined literature mining and microarray analysis: a LMMA approach. Bioinformatics 2006,22:2143-2150);

2) using all network relationships included in published HPRD database, i.e., using HPRD global network;

3) using all network relationships included in published KEGG database, i.e., using KEGG global network.

The above approach 1) of using LMMA-BioNet Biological Network Construction Software developed by the present inventors comprises retrieving from PubMed database relevant abstracts using the disease concerned as key word, determining the genes that appear in the abstracts by matching them with human gene directory retrieved from the website of Committee of Human Gene Nomenclature (http://www.genenames.org/), and searching for relationships among the genes in KEGG database (http:www.genome.jp/kegg/, which records relations of transduction of signals among gene products or metabolism paths) and/or HPRD database (http://www.hprd.org/, which basically records gene products, i.e., physical interactions among proteins).

When using this approach, construction of disease-related gene network can be carried out by a machine (computer), and such construction is an optional step of a method for network-based identification for multicomponent synergistic effect according to the present invention, rather than a necessary stop thereof. That is, construction of disease-related gene network can be either a preparative work to be carried out beforehand or a part of the work to be carried out by a method according to the present invention itself.

Then, calculation of network shortest distances (paths) is performed. Floyd Algorithm, which is known as the most effective way for doing this calculation, is used in a preferred embodiment of the present invention. Other algorithm for calculating network shortest distances, however, can be used. All such alternative embodiments are within the scope of the present invention.

Then, node importance is determined. In an embodiment of the present invention, a value of importance factor IP of each node is determined by performing principal components analysis (PCA) at lease one of a NodeRank value, a Betweenness value, and a Closeness value of each node (definitions and algorithms of these values are described later in the present specification); such principal components analysis (PCA) will be described later in the specification, wherein minimum value normalization is performed on any of the three values used.

Calculation of synergy factor is performed in accordance with Formula (1) given above.

Then, a list is formed for the results based on the above synergy factor; score and listing of a medicine combination indicates the extent of synergy in treating the disease concerned.

Construction of Disease-Related Gene Network:

The present inventors reformed the relations among the genes recorded by HPRD and KEGG into two independent text files, which store the gene relations in HPRD (see http:www.hprd.org/) and KEGG (see http://www.genome.jp/kegg/) respectively; each line in the two files represents one known gene relation. For a pair of genes concerned, a matching was searched in each of the two files; and as long as a line including both genes of the pair of genes concerned was found in any of the two files, it was determined that a relation of interaction existed between the two genes, i.e., that the two genes had an adjacent relation in the gene network being constructed.

As an identical but more practical approach, the above matching was performed inversely. That is, for each pair of genes in HPRD and KEGG databases, it was determined whether both the two genes of the pair of genes concerned appeared in the set of disease-related genes which had been known of the disease concerned.

As alternative embodiments, each of the gene networks of HPRD and KEGG databases was directly used as the disease-related gene network. Effects of the present invention were achieved using each of these different gene networks (as will be explained later).

Calculation of Matrix of Shortest Distances/Paths in Accordance with the Preferred Embodiment of the Present Invention Floyd Algorithm was used.

Floyd alogrithm (also known as Floyd-Warshall algorithm) is a graph analysis algorithm for finding shortest paths in a weighted, directed graph. The Floyd algorithm is an example of dynamic programming. Consider a graph G with vertices V, each numbered 1 through N. Further consider a function $D_{i,j,k}$ that returns the shortest possible path from i to j using only vertices 1 through k as intermediate points along the way. There are two candidates for this path: either the true shortest path only uses nodes in the set (1 ... k); or there exists some path that goes from i to k+1, then from k+1 to j that is better. So, $D_{i,j,k}=\min(D_{i,k,k-1}+D_{k,j,k-1}, D_{i,j,k-1})$.

The above-mention matrix series can be obtained by iterative method; specifically:

D(i,j):dij(k);

Path(i,j): corresponding to subsequent points of i on path of d(i,j)(k), with a final value of a subsequent point of i on the shortest path from i to j;

inputting weighted adjacency matrix $A=[a(i,j)]n \times n$;

1) initiating values
for all i,j,d(i,j)=a(I,j); when a(i,j)=infinite, path(i,j)=0, otherwise path(i,j)=j; k=1;
2) updating d(i,j), path(i,j)
for all i,j, if d(i,k)+d(k,j)>=d(i,j), go to 3); otherwise d(i,j)=d(i,k)+d(k,j), path(i,j)=path(i,k), k=k+1, continuing with 3);
3) repeating 2) until k=n+1.

About PCA method and related parameters:
NodeRank:
NodeRank is an eigenvector corresponding to the maxiumu eigenvalue of network-associated matrix. NodeRank value of node A was determined by formula:

$$P(A) = \frac{1-d}{N} + d \sum_{v \in L_v} \frac{P(v)}{N_v}$$

where N is the number of all nodes in the network, d is an attenuation factor and is usually set at 0.85, which indicates uncertainty of edges in the network, $L_v$ is the set of nodes that directly connect node A, and $N_v$ is the number of edges of node v.

Betweenness:
Betweenness of a node indicates the number of the shortest paths between all pairs of nodes which go through the subject node. Betweenness of a node of a network provides a very good description of flow rate which the node undertakes. The greater the Betweenness of a node is, the more data packs that flow through it, indicating that the node is more likely to be jammed and becomes a bottleneck in the network.

Denoting the number of shortest paths between any two nodes s and d of a graph as $\sigma_{sd}$ and denoting the number of paths in these shortest paths passing through node w as $\sigma_{sd}(w)$, the proportion of the number of paths in these shortest paths passing through node w to the number of shortest paths between nodes s and d being $$\frac{\sigma_{sd}(w)}{\sigma_{sd}},$$

then Betweenness of node was defined as:

$$C_B(w) = \sum_{s \in V} \sum_{d \neq s \in V} \frac{\sigma_{sd}(w)}{\sigma_{sd}}$$

Closeness:
Closeness is a measure of importance of a node. Closeness of a node v was defined as the inverse of the sum of the shortest paths from the node to each of all other nodes in the network:

$$C(v) = \frac{1}{\sum_{t \in V} d_{v,t}}$$

where V is the set of nodes in the network that communicate to node v, and $d_{v,t}$ is the shortest path from node v to node t.

Principal Components Analysis (PCA):

A practical example of application of PCA in the present invention is given below.

Embodiment 1

The present inventors applied a method of network-based identification of multicomponent synergy (NIMS method) of the present invention to selection of medicine combinations for anti-angiogenesis. Selection was made among 63 medicines, which formed 63*(63−1)/2=1953 medicine combinations.

Among these combinations, two had been known as medicine combinations having anti-angiogenesis synergistic effect: 5-fluorouracil+Vinblastine, and 5-fluorouracil+Rapamycin. In a predication by NIMS method for all the 1953 combinations, these two medicine combinations ranked among the top three in ranking of synergistic effect (see Table 1), no matter which of the three gene networks described above (disease-related gene network constructed by the method proposed by the present inventors, HPRD global network, and KEGG global network) was used. These results showed that the NIMS method of the present invention was effective in determining and/or identifying medicine combinations with synergistic effect.

TABLE 1

NIMS synergistic effect ranking of 5-fluorouracil + Vinblastine and 5-fluorouracil + Rapamycin in 1953 medicine combinations

| | | Synergistic effect ranking of 5-fluorouracil medicine combinations by NIMS method | |
|---|---|---|---|
| gene network | | 5-fluorouracil + Vinblastine | 5-fluorouracil + Rapamycin |
| Disease-specific network | Angiogenesis network | 2 | 3 |
| Global network | HPRD global network | 1 | 2 |
| | KEGG global network | 2 | 3 |

Cell Proliferation Verification on Results of NIMS Method

Using NIMS method of the present invention, the present inventors determined scores of synergistic effect of five medicine combinations: sinomenine+luteolin, sinomenine+quercetin, sinomenine+honokiol, sinomenine+matrine, and sinomenine+paeoniflorin. Further, the present inventors verified the results of the scores of NIMS method of the present invention by Cell proliferation verification experiments.

Cell proliferation verification experiments: Human Umbilical Vein Endothelial Cells, HUVEC was purchased from Cascade Biologics. Culture medium containing 2% low density of fetal bovine serum and 5 ng/ml of bFGF M200 culture medium was used in cell culture; incubation of culture was carried out under 37° C. and 5% $CO_2$ environment; passage culture was carried out at 1:2 passage ratio using pancreatin/EDTA as assimilation liquid. HUWECs of 3th-6th generations were used in all the experiments. Small molecule standard substances of sinomenine, luteolin, quercetin, honokiol, matrine, and paeoniflorin were purchased from National Institute for the Control of Pharmaceutical and Biological Products. Density, dosage, and combination ratio of each small molecule and medicine combination were designed on the basis of the description of relevant references.

DMSO hydrotropy was used for sinomenine, luteolin, quercetin, honokiol, and paeoniflorin, while matrine could be directly dissolved in culture medium. Each medicine was preserved under −20° C. environment as a mother liquor with a final concentration of 50 mM. Extent of cell proliferation was evaluated using the Cell Counting Kit CCK-8 developed by DOJINDO Laboratories. Specific experiment steps included performing 24 hour cell proliferation, adding two medicines separately and in combination into 96 orifices, adding 10 microlitres of CCK-8 reagent to each of the orifices 48 hours after pharmacologic intervention, and then incubating the 96 orifices for 4 hours under 37° C. followed by OD value measurements; each group of experiments were repeated for three times.

FIGS. 1a-1e illustrate experiment data for sinomenine and matrine (SM), sinomenine and honokiol (SH), sinomenine and luteolin (SL), sinomenine and quercetin (SQ), and sinomenine and paeoniflorin (SP), respectively, where each gray line indicates inhibition ratio of the medicine combination concerned to HUVEC cell proliferation (curve of dosage dependency) and each black line indicates corresponding curve of Bliss additive effect.

Comments: by this study, the inventors regarded any low-dosage combination with an inhibition ratio greater than 70% as an effective combination, and the inventors evaluated synergistic effect using dosages and combination ratios, Bliss additive effect model, and maximum inhibition ratio reported in pharmacal references. Whether a medicine combination had synergistic effect was determined using Bliss additive effect model. To further evaluate intensity of synergistic effect, the inventors used formula $MIIR=\max(IR_{syn}-IR_{add})$ to calculate maximum increased inhibition rate, MIIR, where $IR_{syn}$ and $IR_{add}$ respectively represent measured inhibition ratio and added inhibition ratio of the medicine combination concerned.

Figure 1:
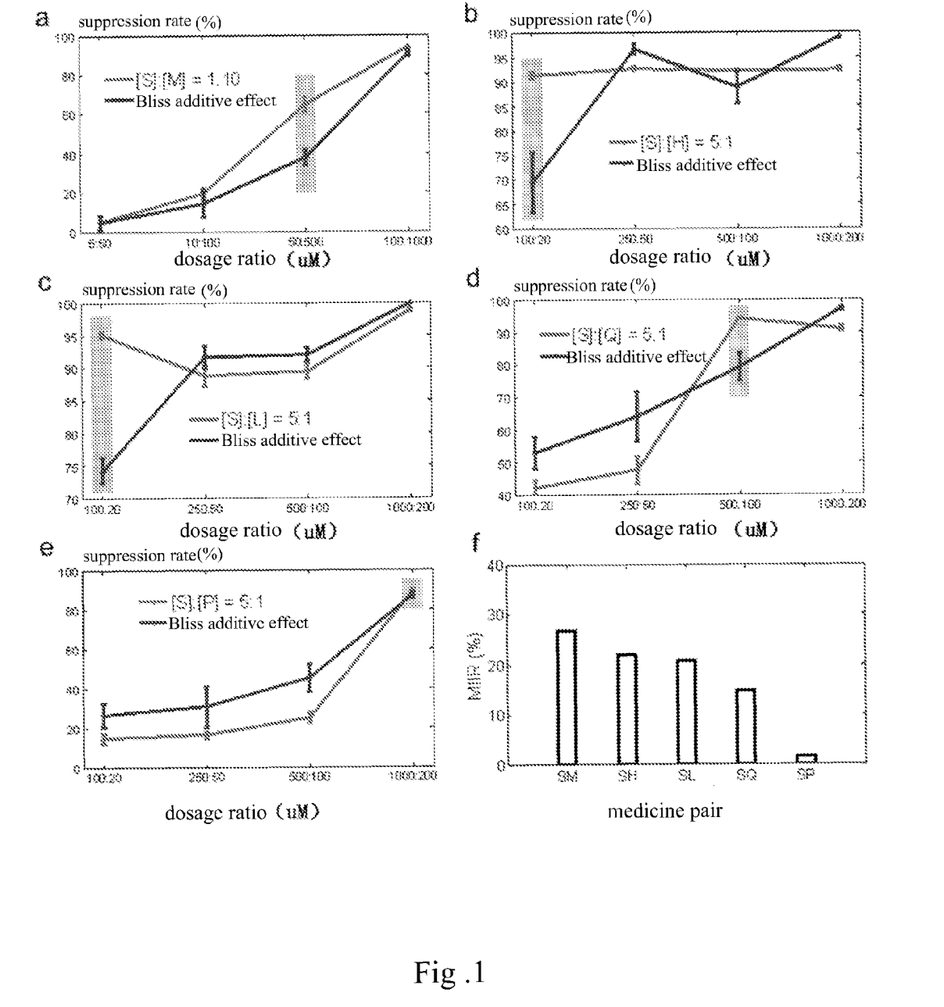

FIG. 1f shows score of maximum increased inhibition rate (MIIR) of each of the five medicine pairs, which indicates extent of synergistic effect, wherein maximum synergistic effect ratio of each medicine combination is indicated by a histogram. It can be seen from FIG. 1f that MIIR score of each of the five medicine pairs is in consistent with the ranking of NIMS predication.

Result analysis: by comparing results of cell experiments and those of NIMS prediction (Table 2), it was shown that ranking resulted from results of cell experiments were fully consistent with results of synergistic effect intensity determined by NIMS prediction based on gene network, so the reliability of NIMS method of the present invention was verified. Also, using NIMS method of the present invention, the inventors found three sinomenine medicine combinations having relatively strong synergistic effect as anti-angiogenesis effective components, including: sinomenine+matrine (MIIR=26.83%), sinomenine and honokiol (MIIR+22%), and sinomenine and luteolin (MIIR=21%). The medicine combination of sinomenine and paeoniflorin, which ranked last in NIMS ranking and cell experiment verification, yielded an MIIR of only 1.86%, indicating that it had little synergistic effect.

The present inventors further investigated the robustness of NIMS method of the present invention with respect to the gene network used. For this, the present inventors made predictions using each of the three networks respectively, which resulted in basically the same outcomes, as showed in Table 3. In terms of prediction accuracy, results obtained by using disease-related gene network (angiogenesis network) and HPRD global network respectively were better, while result obtained by using KEGG global network was relatively inferior.

The present inventors also investigated the robustness of NIMS method of the present invention with respect to the parameters (NodeRank, Betweenness, and/or Closeness) involved, with results as shown for example in Table 2. In Table 2, the $3^{rd}$ column from the left shows the results where all of NodeRank, Betweenness, and Closeness were included in NIMS method of the present invention, while the $4^{th}$ column from the left shows the results where only Betweenness and Closeness were included in NIMS method of the present invention.

TABLE 2

Prediction scores of synergistic effect of medicine combinations including Sinomenine by NIMS Method based on angiogenesis network

| Ranking | Medicine combined with Sinomenine | Synergistic effect score by NIMS prediction | | Cell experiment MIIR value |
|---|---|---|---|---|
| | | NodeRank, Betweenness, Closeness | Betweenness, Closeness | |
| 1 | Matrine | 0.10923 | 0.117280 | 26.83% |
| 2 | Honokiol | 0.10142 | 0.112270 | 22% |
| 3 | Luteolin | 0.10007 | 0.105980 | 21% |
| 4 | Quercetin | 0.09835 | 0.104840 | 15% |
| 5 | Paeoniflorin | 0.082148 | 0.084320 | 1.86% |

TABLE 3 ranking of prediction by NIMS method of synergistic effect of medicine combinations including Sinomenine using three different gene networks

| Medicine combining with Sinomenine | Ranking of synergistic effect by NIMS | | |
|---|---|---|---|
| | Angiogenesis Network | HPRD Global Network | KEGG Global Network |
| Matrine | 1 | 2 | 1 |
| Honokiol | 2 | 1 | 3 |
| Luteolin | 3 | 3 | 4 |
| Quercetin | 4 | 4 | 2 |
| Paeoniflorin | 5 | 5 | 5 |

Steps of an Embodiment of NIMS Method:

In the instance where angiogenesis network was used, computation of NodeRank, Betweenness, and Closeness in NIMS method and PCA were carried out as follow:

(a) The angiogenesis network that the present inventor constructed in a method of construction of disease-related network as described above was a connected sub-network containing 1893 gene nodes and 7598 edges. Data of the angiogenesis network are available and downloadable at: http://bioinfo.au.tsinfhua.edu.cn/member/nzhang/download/angiogenesis.txt (b) NodeRank, Betweenness, and Closeness of each of these nodes were calculated in accordance to the above definitions of these parameters. To ensure comparability among the data, they were normalized by dividing their respective minimum. Thus, a 1893*3 matrix (denoted as Matrix A) was obtained. Matrix A is given in the part of this specification subtitled "Part I: Noderank-Betweenness-Closeness values of Angiogenesis Network", where the three values contained in the i-th pair of parentheses are the NodeRank, Betweenness, and Closeness values respectively of the i-th gene listed on webpage: http://bioinfo.au.tsinghua.edu.cn/member/nzhang/download/angiogenesis.txt (c) PCA (principal components analysis) on the three 1893*1 vectors, constructed by the three columns of Matrix A respectively, was conducted in MATLAB. Denoting IP as final node importance factor vector, then its commands in MATLAB were:

[COEFF, SCORE]=princomp(*A*);*IP*=−*A**COEFF(:,1)

Of course, the IP values can be obtained by conducting PCA operation on any two of the three vectors.

When, for example, only Betweenness and Closeness were taken for PCA operation, and denoting the associated 1893*2 matrix as Matrix C, then its corresponding routine in MATLAB was:

[COEFF, SCORE]=princomp(*C*);*IP*=−*C**COEFF(:,1)

As in an embodiment of the present invention, the present inventors applied NIMS method in the following way (taking medicine combinations of Sinomenine-Matrine, Sinomenine-Honokiol and/or Sinomenine-Luteolin as illustrative examples):

First, IP value a gene relating to a medicine was the IP value of the corresponding node (gene) in the disease-related network. IP values of genes relating to sinomenine, matrine, honokiol, and luteolin respectively are given in the parts of this specification subtitled "Part II" to "Part V" respectively.

(d) Then, on the basis of matrix of shortest paths of the angiogenesis network, a matrix of shortest paths among genes for each of the pairs of medicines including sinomenine was obtained. A matrix of shortest parts among genes for each of medicine pairs Sinomenine-Matrine, Sinomenine-Honokiol and Sinomenine-Luteolin is given in the parts of this specification subtitled "Part VI" to "Part VIII" respectively.

(e) ST value for each of the pairs of medicines was weighted by a corresponding AS value (Sinomenine-Matrine: 0.17075, Sinomenine-Honokiol: 0.15897, Sinomenine-Luteolin: 0.17050) to obtain a final value of synergy factor S (Sinomenine-Matrine:0.10923, Sinomenine-Honokiol: 0.10142, Sinomenine-Luteolin: 0.10007).

(f) These pairs of medicines were ranked according to the above results of synergy strength of each of them.

Figure 2:
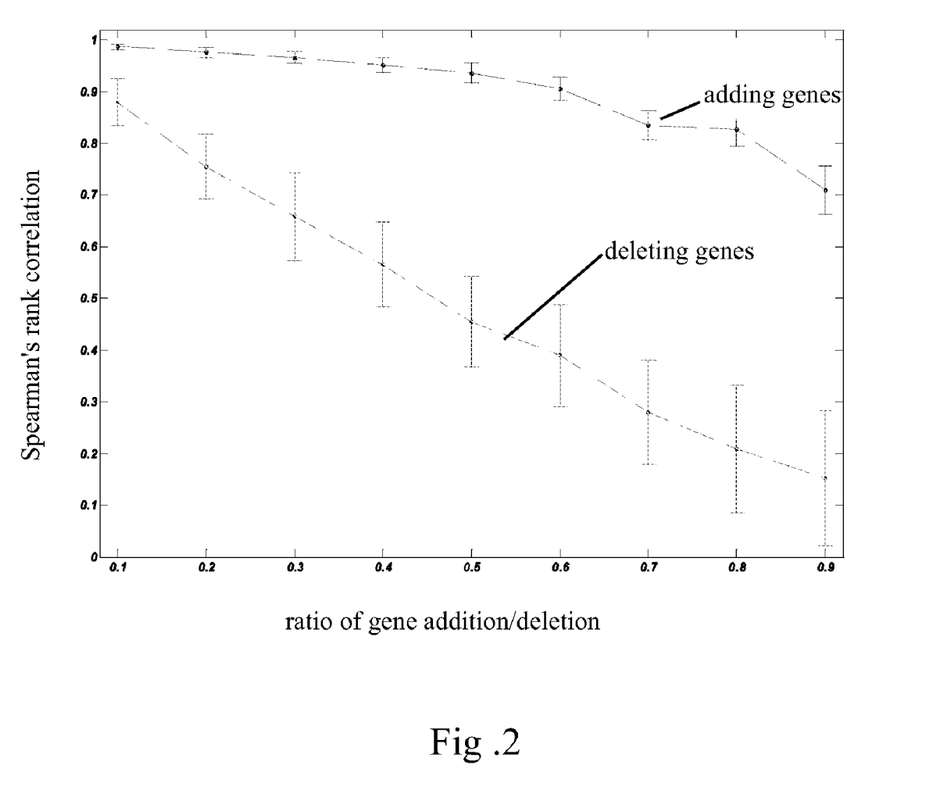
FIG. 2 is a diagram for illustrating robustness of a method of network-based identification of multicomponent synergy according to the present invention.

On Robustness of NIMS Method with Respect to Random Addition/Deletion of Medicine-Effective Genes In collecting medicine-effective genes by reviewing references, neglects and/or mistakes in the references can hardly be avoided. The present inventors evaluated the robustness of NIMS method by randomly increasing/decreasing the medicine-effective genes, and described the robustness evaluation by comparing Spearman rank pertinence before and after permutation, and obtained the results as shown in FIG. 2. As the results (as shown in FIG. 2) indicated, effect of random addition of genes on result of NIMS method was not obvious, while effect of random deletion of genes on result of NIMS method was relatively remarkable; however, even when the number of genes was deleted by 50%, the pertinence of NIMS result to the NIMS result without gene deletion still reached 50%. The above experiment outcomes indicated that NIMS method of the present invention had strong robustness to collection of medicine-effective genes.

It is to be understood that the description given above is for disclosure, rather than limitation, of the present invention, and various arrangements, modifications and/or changes can be made to the embodiments described above without departing from the scope of the present invention.

Part I: Noderank-Betweenness-Closeness Values of Angiogenesis Network (Matrix A)
(28.304,29.846,2.7015); (1.2325,1,1.7449); (24.564,22.378, 2.541); (1.2257,1,1.7447); (2.0985,1.0421,1.9812); (1.826, 1.0112,2.0015); (2.2416,1,1.6851); (2.0573,1.4359,2.1775); (4.6517,3.0379,1.7682); (3.4778, 1.1472,2.3706); (3.9337, 1.1581,1.9943); (38.952,33.064,2.8982); (3.3814,2.5698,1.9309); (1.5289,1,1.9501); (1.0724,1,1.9262); (5.4903,3.7287,2.0068); (9.1525,3.625,2.4496); (15.469,5.6757,2.5692); (4.6133, 2.6714,2.068); (12.307,4.2026,2.3747); (3.1998,1.1501,1.8779); (6.4805,3.7035,2.1668); (3.0421,1.2686,2.124); (8.0527,1.6802,1.9328); (5.3362,2.4403,2.0612); (5.1311,4.0996,1.9438); (4.5309,1.1234,2.3687); (3.8859,1.1694,1.7156); (1.4309,1, 1.6823); (4.1645,1.3791,1.7071); (2.2703,1.3173,2.0826); (1.3369, 1,1.7451); (1.9414,1,1.4263); (1.1335,1,2.1322); (14.095,6.4194,2.378); (3.7074,5.548,2.193); (15.486, 7.3526,2.6097); (1.0464,1,2.1145); (6.0541,1.2202,1.8854); (2.7165,1.2,1.8628); (6.0701,2.9979,1.4297); (7.0989,2.8667,2.2514); (1.3127,1,1.6808); (1.6399,1.0176, 1.7724); (7.0334,2.7518,2.236); (3.2205,1.2792, 1.9291); (5.8846,4.1141,2.2384); (6.1965,2.7663,2.3947); (6.9995,4.4391,2.4193); (17.786,9.0719,2.5815); (1.1212,1, 1.9316); (6.2869,2.4204,1.9626); (2.1177,1.0803,2.1609); (10.208,3.6215,2.4799); (3.6106, 1.1189,2.1747); (1.2626,1, 1.7697); (8.4619,3.3604,2.4358); (1.4636,1,1.6027); (5.5471,4.131,2.3624); (26.389,16.534,2.7565); (2.0032,1.0023,1.9368); (2.2835,1.1076,1.9794); (3.3908,2.309,2.1228); (5.0891, 2.0201,2.1728); (1.2489,1, 1.7544); (8.3371,6.17,2.2873); (1.4766,1,1.6405); (6.9743, 1.6134,2.1103); (3.6729,1.2107,2.1388); (4.0415,1.3411,2.3432); (3.738,1.0147,2.3162); (5.4189,1.4332,2.3259); (5.9447, 3.0432,2.3863); (5.2243, 3.0499,2.3277); (1.7853,1,1.6639); (1.9881,1,1.2274); (1.3043,1,1.6992); (1.6554, 1,1.5048); (2.7575,1.4891,2.2036); (3.2597,1.3797,1.9463); (4.3039,2.9837,2.2072); (2.0251,1.4049, 2.02); (4.9476,1.8792,2.1498); (3.3176,1.5054,1.989); (1.3064,1,1.6471); (1.0712,1,2.1151); (12.261,9.3364, 2.4158); (2.7549,1.1276,2.0328); (1.0961,1,2.0023); (5.4327,3.1294,2.0444); (1.2562,1,1.7747); (5.1927, 3.0036, 1.6167); (15.259,12.342,2.3241); (1.5148,1.0015,1.884); (8.7888,3.2494,2.3981); (4.2793,1.1514, 2.1529); (4.1271, 2.435,2.0737); (3.121,2.0681,2.2454); (5.0179,2.8864,2.2301); (1.291,1,1.6604); (12.273, 10.813, 2.1331); (1.3765,1,1.6098); (2.7841,1.0205,2.0422); (3.6895,1.5383,2.2457); (1.4859,1,1.6584); (1.8919,1.0263, 2.2511); (1.1883,1,1.8861); (1.6719,1.0024,1.8793); (2.7529,1.1509,1.9721); (1.831, 1.0003,1.6927); (5.3596,3.9649,1.641); (2.0986,1.0067,1.9341); (4.4589,2.5125,1.8868); (2.2027,1.021, 2.1557); (1.9325,1, 1.4136); (13.408,4.3841,2.3962); (2.2504,1.2352,1.998); (1.6824,1,1.3849); (1.6388,1.039,2.0159); (2.3948,1.1932,1.5444); (2.4824,1.0425,2.0224); (5.0687,2.9388,2.3962); (3.3464,1,1.3014); (15.236,9.7939, 2.6184); (1.3734,1,1.6477); (3.975,3.57,1.9301); (16.151,6.5691,2.5419); (2.2352,1.1069, 2.0575); (20.889, 12.899,2.7054); (1.604,1,1.4132); (7.461,3.8938,2.1731); (1.0741,1,1.7231); (1.365,1, 1.6714); (5.6803,3.3867,2.1731); (2.8509,1.0225,2.0195); (4.2876,1.883,2.066); (4.1552,2.2374,2.204); (7.0539,5.7621,2.2205); (4.192,1.6853,2.2444); (3.9513,1.7254,1.9631); (1.441,1,1.272); (5.8707,2.234,2.4228); (2.2236,1,1.6877); (4.1054,3.3029,2.2602); (1.9736,1.006,1.9494); (3.6496,1.0249,2.1841); (2.2352, 1.043,1.6316); (6.9391,1.3929,1.7888); (24.989,11.23,2.5846); (4.8474,2.9974,1.4526); (1.1479,1,1.8954); (1.1594,1,1.7783); (3.6496,1.0249,2.1841); (1.5064,1.006,2.0927); (3.7341,2.1,1.9232); (1.4769,1,1.557); (2.5605,1.0888,1.9433); (1.3349,1,1.7245); (1.0942,1,2.0522); (4.1058,1.6685,1.9448); (6.7117,2.4615, 2.4201); (8.3156, 1.7904,2.2447); (2.4772,1.1507,1.9406); (19.157,22.035,2.5679); (6.5662,2.4324,2.2626); (5.032,1.3697,1.4888); (7.0874,1.6887,2.2504); (12.996,10.275,2.4429); (1.8236,1.4653,1.9964); (5.127,1.983,2.2153); (1.3884,1,1.6039); (2.7774,1.0793,1.9822); (3.2477,1.5308,2.1204); (1.6611,1, 1.4267); (1.4458,1,2.1791); (1.3522,1,1.6778); (3.2357,1.1063,2.2694); (5.5465,2.4101,2.0606); (18.854,4.8555, 2.5653); (2.2127,1.3231,1.7145); (3.4238, 1.9992,1.4134); (2.2194,1.2201,1.7356); (7.8629,4.2964,2.0832); (4.2065,1.8364,2.1181); (4.6977,1.7286,2.0116); (4.8928,1.5159,2.2595); (6.2976,3.9021,2.1083); (1.7415,1,1.7059); (1.1244,1,1.755); (3.5176,2.0178,1.6767); (8.5014,4.7542,2.2261); (1.543,1.0083,1.9641); (3.582,2.292,2.068); (7.7272,2.5445,2.3886); (4.5698,1.0707,2.2575); (4.4494,2.0209,2.3141); (3.4908,1.3308,1.8279); (10.592,2.2365,2.3803); (5.0907,2.5392,2.2626); (7.4515,4.0803,2.4046); (5.3556, 1.4903,2.3583); (1.6666,1.0986,2.0298); (3.0664,1.6008,2.0323); (2.0177,1.6304,1.9527); (1.5289,1, 1.9501); (1.7622,1.3533,2.1416); (2.0276,1.0213,1.6716); (7.2268,7.4736,2.475); (5.2265,2.4507,2.0181); (1.2039,1,1.6821); (6.1809,1.7761,2.4016); (2.0704,1.0428, 1.9814); (4.2889,1.4684,1.5924); (1.7948,1.0074, 2.1684); (1.579,1.0433,2.241); (3.1747,2.8064,1.7143); (3.819,1.2479,1.9817); (6.6823,4.3232,1.6279); (2.2491,1.0098,1.7888); (2.4149,1.1246,2.1385); (1.101,1,1.6975); (2.0046,1.0231,1.9532); (1.5959,1, 1.683); (1.9697,1.0055,2.1041); (5.3797,1.9163,1.5625); (2.1347,1.0015,1.7633); (3.6376,3.6449,2.2222); (2.815,1.089,1.9567); (4.1676,1.097,1.6223); (5.018,3.2041,2.3381); (3.1022,1.2583,2.1918); (5.1572,3.174,1.8646); (1.8635,1.0116,1.7424); (2.5752,1.0594,2.0268); (5.4484,2.6595,2.1825); (1.5158,1.0115, 2.0835); (15.115,9.8137,2.1535); (2.2897, 1.0009,1.7823); (4.4778,1.0079,1.8171); (8.0355,6.4172,2.0279); (1.9094,1.0044,1.7499); (1.6728,1.0002,2.0023); (2.6733,1.0495,1.5687); (1.0804,1, 2.0192); (5.8155, 3.189,2.4588); (1.1883,1,1.8861); (1.1286, 1,1.8169); (1.3043,1,1.6992); (1.5466,1,1.5366); (2.5622,1.0985, 1.8875); (5.7185,1.7317,2.202); (1.3938,1, 1.728); (5.1396,1.1316,2.2531); (1.7139,1,1.2455); (1.9751, 1, 1.2412); (6.0998,2.3783,2.3553); (9.133,3.0028,2.3169); (2.1047,1.0526,1.7937); (3.3663,1.2138,1.9549); (4.9364,2.4265,2.2176); (4.3203,1.4961,2.3291); (6.1006,1.4973,2.1991); (2.6048,1.035,1.5428); (1.3349, 1,1.7245); (1.2821,1,1.5982); (3.7968,2.422,2.0087); (2.8212,1,1.7867); (4.7016,2.5161,2.0916); (3.4155, 2.1455, 2.1772); (2.5562,1.2639,2.1765); (2.3381,1.2762,2.2633); (2.0621,1,1.6952); (1.0465,1,1.829); (1.2358,1,1.6219); (1.5378,1,1.542); (5.0725,1.0134,2.1653); (1.2067,1,1.6953); (4.7123,2.4805,2.34); (1.2664,1,1.7096); (3.1791,1.5948,1.6062); (4.8456,2.1749,1.9595); (5.6345,4.6418,1.7745); (2.6473,1.243,1.884); (2.3764,1.594,2.0646); (4.8053,1.7683,1.8434); (2.3875,1.0354,1.9888); (6.8388,1.4614,2.4856); (1.9024,1.028,1.7888); (5.1498,3.4612,2.1207); (5.3436,2.7266,2.2531); (1.5258,1,1.7123); (12.104, 5.4543, 2.4275); (4.5125,1.8952,2.2926); (10.737,11.167,2.2839);

(6.3475,1.8615,2.2877); (2.5564,1.3877, 1.8734); (1.8803,1,1.392); (12.052,7.9716,2.2481); (1.3057,1,1.5807); (2.2552, 1.3475,1.776); (6.5076, 2.299,1.9208); (2.9794,1.1869,2.0475); (4.0236,2.9974,1.3353); (1.3612,1, 1.4348); (2.0531,1.0112,1.9112); (3.2451,1.3875,2.2182); (1.1063,1,1.8262); (1.134,1,1.7467); (1.7228,1.1836,1.8916); (1.5969,1,2.1452); (1.9234,1.0608, 1.8304); (2.6246,1.9992,2.066); (5.1549,2.0896,2.1905); (3.3784,1.0092,1.8064); (18.997,12.286,2.6633); (2.0243,1.0116,1.9988); (12.042,3.992,2.3262); (16.406,8.4075,2.3031); (2.1347,1.0015,1.7633); (4.6741,6.0081,2.0068); (12.394,4.3724,2.3863); (1.3034,1, 1.7989); (1.2495,1,1.6781); (2.2536,1.0344,2.1053); (1.2255,1,1.803); (3.7461,2.035,1.8322); (4.973,4.0354,2.1056); (2.4805,1.2319,1.9338); (1.1936,1,1.6872); (2.0623,1.1916,1.8623); (29.049,27.518, 2.8158); (3.5526,2.2603,2.1934); (4.7793, 1.3758,1.8861); (8.1677,3.8815,2.336); (3.1713,1.1221,2.2698); (2.4149,1.1246,2.1385); (3.0582,1.2992, 1.7061); (2.1204, 1.0071,1.6701); (3.6288,1.8575,2.0663); (1.3281,1,1.5664); (5.7104,1.8418,2.236); (2.8017,1.9992,1.6957); (1.9813,1.5371,1.8454); (1.6902,1,1.1186); (1.2947,1,1.7188); (22.256,17.571,2.6723); (1.683,1.0385,1.9846); (2.3734,1.0051,1.9451); (1.1335,1,2.1322); (1.5703,1,1.9064); (6.3658,3.1673, 1.7164); (1.0272,1,1.9391); (2.1293,1,1.3017); (2.8856,2.0035,2.07); (1.0328,1,1.8563); (1.2085,1,1.8127); (3.066,1.0003,1.1557); (3.022,2.1824,1.7125); (2.78,1.3091,2.0878); (3.4529,2.1976,2.1352); (3.3974, 1.7947,2.2075); (5.1631,2.9478,1.9383); (1.3239,1,1.5216); (8.3408,3.4257,2.038); (5.8407,2.9715, 2.4069); (3.1497,1.018,2.1443); (3.4803,1.1018,2.1634); (2.3969,1.0945,1.5568); (1.9011,1.0311,1.7695); (2.0959,1.0082,1.6079); (3.6573,2.1306,2.1328); (1.5591,1.0119,2.0464); (1.9577,1,1.7487); (4.0117,1.9467, 2.2127); (5.0143,2.7821,2.1921); (8.4847,6.0317,1.6982); (2.6683,1.0291,1.9479); (2.2929,1.0933, 1.6348); (5.8214, 2.8923,2.1841); (5.8243,2.0875,1.919); (5.2707,3.7734,1.9368); (1.0961,1,2.0023); (1.4934, 1,1.4323); (1.9598,1,2.1012); (18.155,8.1451,2.5509); (1.8753,1,2.1972); (1.7817,1,1.5107); (5.6034, 1.7595,1.5247); (1.8017,1.0136,1.7055); (9.1221,5.6783,2.4783); (1.3385,1,1.5988); (1.2626,1,1.7697); (3.0185,1.0518,1.9534); (6.9501,5.6803, 2.3465); (3.1575,1.0216,1.8375); (1.5691,1.0062,1.8809); (2.1741, 1.0201,1.8699); (17.366,5.7295,2.5785); (3.04,1.0397,2.1615); (1.8188,1.0003,2.2101); (2.7921,1.8991, 2.2062); (1.0326,1,1.9964); (2.8746,1.0719, 2.0071); (2.5497,1.0665,1.8456); (2.0156,1.2511,2.1696); (10.834,3.601,2.2894); (3.3988,1.2553,2.2626); (4.4499,2.3653,2.1784); (6.4854,1.7304,2.2957); (1.7984, 1.0076,2.1458); (1.7892,1,1.3438); (1.2006,1,1.8835); (2.1347,1.0015,1.7633); (4.0551,1.7287,2.2619); (1.4077,1, 2.0809); (3.7232,2.1421,1.9356); (5.7221,3.5427,1.5552); (1.1136,1,1.9127); (6.1567,3.0398,2.11); (9.3992,5.4395,2.3698); (4.1876,2.6926,2.0971); (7.6335,3.4533,2.359); (4.5036,1.3335,2.1507); (4.209,2.2738,1.9996); (1.6344,1.0046,1.9319); (5.545,2.7976,1.695); (2.4642,1.1683,2.1391); (4.6282,3.1452, 2.4154); (2.3398,1.0823,1.6453); (1.642,1.0006,1.7429); (4.5701,1.3102,2.3151); (3.6407,1.559,2.1765); (3.9714,2.2589,2.3996); (2.3604,1.0314,1.5501); (6.9874,3.2887,2.1409); (11.042,8.0621,2.3799); (2.5939,1.0337,1.9718); (1.606,1.02,1.9875); (1.4113,1,1.5715); (2.9335,1.9992,1.7188); (1.0772,1,2.0455); (1.3734,1,1.6477); (2.1499,1.008,1.49); (2.4947,1.0162,2.2701); (4.1828,1.1267,2.1921); (5.1963,1.7992, 2.1715); (4.1332,2.2649,2.0087); (2.102,1, 1.2431); (6.4136,2.0553,2.344); (8.7143,4.5835,2.4178); (5.1396,4.7831,2.0881); (3.9049,1.3323,1.9494); (1.5823,1.0023,1.8117); (2.4089,1.0132,2.2004); (3.6496, 1.0249,2.1841); (2.713,1.2021,1.7802); (3.1462,1.27,2.2156); (2.8439,1.1134,2.0522); (4.5627,1.3171,2.0157); (2.7198,1.1892,1.7506); (1.8385,1.0171,2.0677); (3.2297,1.0001,1.4774); (1.9731,1.0012,1.9867); (1.8051,1.0001,1.479); (8.3441,2.7863,2.2052); (1.2562,1,1.7747); (2.6246,1.9992, 2.066); (2.0671,1.0126, 1.7483); (1.2527,1,1.7225); (3.0727, 1.493,2.0814); (5.1041,2.5741,2.1628); (2.1006,1.0716,2.1258); (5.3748,1.8385,2.2894); (4.6634,1.9992,1.1437); (3.4953,1,1.4762); (9.4314,4.0807, 2.3363); (2.401,1.039, 1.3314); (3.4257,1.3906,1.9854); (2.4833,1.0001,1.2554); (7.6461,3.4949,2.0609); (4.8171,2.2516,2.3432); (2.4699,1.0948,1.8217); (1.5071,1, 2.1902); (4.1869,2.8811,2.082); (1.2828,1,1.6908); (2.4117, 1.067, 1.7046); (1.9806,1.0552,2.0592); (6.069,5.0018,1.8073); (2.1663,1.0136,1.7402); (2.9992,1.5685,2.0884); (1.6078,1,1.4615); (2.4455,1.0573, 1.8138); (1.8012,1,1.6403); (6.9538,3.0005,2.4318); (3.0383,2.0469, 1.9042); (1.9136,1,2.1425); (3.3322,1.9992, 1.4732); (3.5833,1.6214,2.1825); (7.1679,1.9107,2.3066); (1.4588,1,1.412); (5.8057,1.7236,1.6527); (6.5691,2.1289,2.4726); (4.1057,1.6037,1.8901); (3.0317,1.0417, 2.236); (4.4465,4.2433,1.803); (4.269,2.6541,2.1507); (1.3837,1,2.1243); (9.5304,3.7026,2.4464); (3.6301, 2.001,2.268); (2.8668,1.0445,2.203); (4.3778,1.3646,1.9946); (2.4429,1.3221,2.0754); (1.2909,1,1.7184); (2.5929,1.135,2.1297); (17.527,9.8297,2.3905); (1.0975,1,2.0542); (5.8505,5.3883,1.8114); (1.1081, 1,1.8713); (1.1335,1,2.1322); (3.9162,1.3969,2.0592); (1.2672,1,1.7273); (5.1714,4.5231,2.0843); (1.1684, 1,1.7846); (2.8687,2.0892,2.1222); (1.1759,1,1.7764); (18.755,8.0872,2.5967); (4.5081,1.1057,1.9134); (5.4436,3.3236,2.2111); (3.1041,1.6179,2.2863); (2.2257,1.2088,1.7899); (3.0393,1.0501,1.9269); (3.883, 1.5318,2.2127); (4.5834,2.105,2.0869); (3.9275,2.954,2.1258); (1.7159,1.0009,1.873); (1.693,1.0275,1.8681); (15.386,6.3955,2.6732); (4.0316,1.6974,2.0598); (1.5724,1.0026,1.8371); (2.2416,1, 1.6851); (3.5053, 1.484,1.7241); (9.4197,3.8632,2.3561); (4.3592,1.0504,1.5597); (4.0042,1.5293,1.5789); (4.4465,1.6078,2.3144); (11.737,7.9617,2.3627); (2.3537,1.0122,1.9188); (4.5891,1.3747,1.5929); (1.1323,1, 1.9321); (1.6298,1.0151,2.0162); (43.73,33.349,2.7651); (3.6496,1.0249,2.1841); (1.8698,1,1.1691); (5.8105,1.8817, 2.1285); (3.3624,1.4363,1.8436); (1.8299,1,1.5323); (5.0686,2.1872,2.3041); (3.8418,1.4813,1.9144); (1.1944,1, 1.8589); (3.8363,1.1892,1.8293); (2.7529,1.0541,1.7318); (7.0241,5.4145,2.4275); (4.983,4.077,2.1914); (4.3814,2.0424,2.1027); (6.1314,1.9749,2.0863); (5.684,3.4185,2.186); (1.5096,1.0048,1.9595); (2.6116,1.0728,2.0708); (1.2083,1,1.7827); (37.297,31.797, 2.7686); (7.0622,4.2476,2.151); (17.066, 5.6075,2.5557); (1.8709,1.0717,1.8746); (17.703,6.4704,2.5705); (2.1436,1.0978,1.9675); (4.9058,4.4217, 2.3443); (1.7703,1, 1.9595); (4.4842,1.5641,2.0983); (5.1355,1.4512,2.4042); (14.698,5.6875,2.4209); (4.4178,1.6107,2.0697); (4.6907,2.3494,2.2701); (5.5259,3.1486,1.9132); (1.2607,1, 1.7802); (3.1219,1.1233, 1.8402); (3.3055,1.4311,2.1343); (4.213,2.8196,2.2957); (3.2209,1.0461,2.2017); (1.315,1,1.7532); (27.03,27.96,2.8063); (2.9703,1.2351,2.2497); (3.4223,2.0945,1.8556); (1.4572,1, 2.0079); (2.6287,1.3593, 2.1222); (2.4989,1.1741,1.4916); (1.7635,1.0242,1.9168); (15.391,8.3992,2.4836);

(2.2803,1.0211,1.6005); (2.2339,1.0282,1.7618); (2.3561,1.0309,1.6896); (1.1321,1,1.9499); (7.884,6.4156,2.2248); (5.2885, 2.5651,2.4653); (3.2447,1.0457,1.5824); (1.4444,1,1.5307); (1.7177,1,1.5461); (1.8918,1,1.7459); (1.5604, 1.0163,1.818); (1.8391,1.0127,2.0751); (1.3734,1,1.6477); (2.4819,1.05,1.7506); (12.127,8.1668,2.3724); (2.319,1.0672,2.1334); (4.1738,1.689,2.2444); (3.9184,1.1105,2.2701); (1.8335,1.0161,1.8536); (3.0161, 1.3137,2.0623); (2.6187,1.6347,1.8093); (1.7827,1.0189,1.8522); (16.739,17.072,2.5846); (3.2379,1.0013,1.4007); (2.0077,1.0004,1.9705); (23.509,30.505,2.7891); (1.7868,1.0072,1.7925); (1.0748,1, 1.8732); (21.456,13.027,2.6747); (5.7118,1.7911,2.2873); (9.748,4.6972,2.3542); (4.438,4.4096,2.0028); (2.4134, 1.8636,2.0812); (18.121,9.0195,2.5176); (1.0505,1,1.9562); (1.267,1,1.7808); (5.2869,1.6521,1.4901); (1.7337,1.0032,2.0731); (1.0961,1,2.0023); (6.5076,2.299,1.9208); (6.1412,1.0781,2.1994); (6.4378,2.5419,2.3784); (2.2474,1.0802,1.9494); (1.1244,1, 1.7684); (7.6329,3.9973,2.1033); (9.4441,3.3854,2.0866); (4.7029,1.8343,2.2528); (13.357,10.043,2.6088); (1.1081,1, 1.8713); (1.8398,1.3407,2.089); (14.93,9.0865, 2.2756); (3.6004,1.0082,1.686); (23.86,20.647,2.723); (3.0199,1.296,1.5533); (14.131,10.669,2.4803); (4.6755,2.3195,2.2548); (8.0775,6.5547,2.0519); (3.7012,2.4507,2.2484); (1.5837,1.0098,2.0184); (2.1156, 1.0079,1.9501); (8.7734,3.362,2.2514); (1.7059,1,1.8463); (3.8494,1.1837,2.1449); (1.2567,1,1.6564); (2.5369,1,1.7662); (3.1923,1.2,2.1361); (3.726,1.103,1.5158); (7.8752,3.9678,2.3173); (5.3621,3.4552,2.235); (3.5299,1.7097,1.6986); (1.1432,1,1.6466); (6.6454,2.2434,2.3396); (18.001,20.205, 2.5557); (2.873, 1.2083,2.0249); (4.959,1.0839,1.4041); (16.298,7.877,2.5118); (1.1286,1,1.8169); (4.9557,3.6216,2.2186); (21.539,13.456,2.7049); (1.7081,1.0975,2.0714); (2.9013,1.0372,2.2278); (1.9439,1.0025,1.9659); (3.292,1.2111,2.2832); (6.6937,2.2966,2.2558); (5.3549,3.0488,1.8951); (1.5426,1.0004,1.9491); (8.3117, 4.0732,1.8672); (4.4836, 2.5298,2.3327); (1.1595,1,1.8534); (4.3447,1.0134,2.0977); (6.0948,1.5253,1.9326); (1.4469,1,1.6415); (1.4293,1.0003, 2.1753); (2.2416,1,1.6851); (4.4425,1.0011,1.5379); (4.793, 2.1145, 2.2444); (1,1,1.9401); (1.6936,1.0111,1.9539); (14.75,5.8706,2.5869); (3.0295,1.4993,1.4513); (8.3573, 3.7099,2.1261); (3.9208,1.4212,2.2808); (1.1508,1,1.8286); (4.974,1.7095,1.9956); (4.9424,1.6355,2.1572); (1.6556,1.0215,2.1455); (1.8071,1.0138,2.0157); (5.0815,1.2487,2.3244); (2.9977,1.9992,1.6573); (2.5331,1.1729,1.7437); (13.898,5.233,2.5067); (2.1555,1.364,1.7787); (4.1334,2.0008,1.9274); (17.279, 6.6851,2.64); (2.7899,1.054,1.8481); (2.2781,1,1.8873); (1.2976,1,1.695); (4.8153,2.0729,2.2787); (1.3394, 1,1.7567); (8.0585,2.3986,2.2711); (1.4024,1,1.7119); (3.1149,1.3407,1.7821); (1.7143,1.1132,2.0068); (4.1443,1.1595,2.2524); (2.5041,1,1.4126); (2.4919,1.0151, 1.5815); (3.9507,1.5629,1.816); (3.6496,1.0249, 2.1841); (1.2503,1,1.7709); (1.8739,1.0174,2.3327); (18.169,14.087, 2.4673); (1.1137,1,1.831); (4.6781, 1.9301,2.3234); (11.95, 2.9194,2.4421); (2.9416,1.0672,1.7398); (5.2563,1.4606,2.3396); (3.0141,1.1804, 2.2075); (1.365,1, 1.6714); (5.8731,3.8929,2.4881); (1.3618,1,1.2994); (1.1573,1,1.8217);(2.1855,1.1674, 1.7352); (6.7707,2.9377, 2.1844); (1.5332,1,2.0697); (1.2409,1,1.2003); (1.4444,1,1.5307); (9.6408,5.2268,2.1921); (3.3753,1.4355, 2.1303); (2.5959,1.8175,1.8937); (1.0644,1,1.7306); (1.0936,1,2.0655); (3.2145,1.4379,2.2985); (5.3528,2.1476, 1.6877); (3.6496,1.0249,2.1841); (5.6549,1.4369,2.3535); (2.7088, 1.1671,1.9827); (2.3768,1.1064,1.8994); (7.0067, 1.2005,2.3557); (15.057,5.6717,2.4385); (5.0283,1.468, 1.994); (9.5439,7.7388,2.6143); (15.978,9.3801,2.5303); (7.9588,4.8626,2.2095); (1.0464,1,2.1145); (23.829,16.561, 2.6671); (2.9068,1.7701,1.959); (5.6826,1.4138,2.1409); (1.1069,1,1.8632); (1.5319,1,2.0907); (1.8299,1,1.5323); (2.2606,1.0801,1.9257); (1.0939,1,1.8322); (8.4539,2.9287, 2.4081); (13.48,4.3218, 2.6266); (2.7233,1.1746,1.9139); (5.9006,3.5902,2.1306); (1.6672,1.0261,2.0933); (2.4234,1.0413,2.1554); (2.5712,1,1.4863); (1.7107,1.062,1.8561); (6.7146,2.603,2.3747); (2.0985,1.0421,1.9812); (6.9735,3.1769, 2.1089); (1.7041, 1.0009,1.8162); (2.0194,1.0281,1.6602); (1.8834,1.0986,2.134); (41.918,37.451,2.8359); (6.2706,3.2497,2.2205); (2.5623,1.098,2.3513); (2.8002,1.4993,1.3517); (1.472,1,2.1388); (9.707, 6.455,2.0777); (4.911,2.9553,2.3826); (1.6583,1.0204,1.7967); (29.616,23.256,2.729); (29.09,19.867,2.6953); (7.0331,2.59,2.2487); (2.4422,1.1883,1.9279); (4.3998,1.7292,2.241); (2.557,1.0918,2.0901); (1.6869, 1.3108,2.0477); (2.3159,1.2663,1.873); (1.3885,1,1.5101); (2.4121,1.0353,1.7772); (10.147,4.07,2.4645); (3.6188,1.5958,2.2612); (4.6293,3.1642,1.9724); (1.7052,1.121,2.1609); (1.8457,1,1.3849); (9.3774, 5.1738, 2.3542); (2.6232,1.0476,1.9443); (3.2521,1.479,2.3155); (4.7805,1.1892,2.2098); (3.5584,1.2202, 2.121); (1.9199,1.0034,1.9188); (1.1089,1,1.8651); (6.5855,1.7778, 2.2853); (2.8448,1.1833,1.9443); (1.299, 1,1.6428); (2.4149, 1.1246,2.1385); (13.854,10.236,2.4697); (5.8041,1.5112,2.3273); (2.4439,1.5082, 1.9557); (2.4123, 1.0432,2.1312); (6.8734,4.6187,2.4077); (4.2121,1.3963,2.1297); (5.0596,2.2369,2.1709); (1.5942,1.049,2.0211); (5.8787,3.3044,2.2825); (7.9946,3.0349,2.4935); (1.9973,1.0028,2.0436); (1.169, 1,1.7294); (1.7209,1,2.1554); (2.016,1.0249,1.7787); (1.9141,1.0207,2.1659); (2.9778,1.0001,1.4112); (1.9987,1.1116,1.8968); (11.538,6.961,2.5457); (3.6504,1.4715,2.0181); (3.5812,1,1.2285); (2.9393,1.1472, 1.8171); (1.2109,1,1.822); (1.0645,1,1.9416); (1.9866,1.3226,1.8951); (4.2729,1.3863,2.1142); (4.918, 3.3479,2.0312); (1.5287,1,1.9804); (2.5487,1.0704,2.0178); (5.6691,2.1974,2.2491); (14.359,10.31,2.294); (4.6709,1.2854,1.4589); (10.512,3.1608,2.5316); (2.0944,1.9004,2.0921); (6.0918,3.1849,2.3487); (4.9644,3.93,2.2708); (1.5606,1.0033,1.8579); (4.4659,1.4547,2.2033); (1.207,1,1.811); (1.2006,1,1.8835); (6.0884,4.3022,2.204); (1.1494,1,1.9346); (1.2006,1,1.8835); (1.2532,1,1.7199); (4.8958,1.09,2.4213); (3.2123,2.0977,2.1343); (6.3486,2.1717,2.1044); (1.1137,1, 1.831); (4.7893,1.5442,2.2982); (9.4227,11.615, 2.5143); (4.094,2.0096,1.6767); (2.505,1.0187,1.7032); (4.0726,3.3956,1.9323); (3.4202,2.1095,2.2059); (2.696,1.0446,1.8279); (1.267,1,1.7808); (1.0975,1,2.0542); (2.2352,1.043,1.6316); (4.8559,3.4452,1.9188); (1.195,1,1.7508); (6.2773,2.3856,2.1578); (2.2816,1.1009,1.9476); (1.2255,1,1.803); (1.9254,1.0209, 1.7414); (8.7928,4.1756,2.1575); (6.9226,3.2726,2.2457); (9.8995,5.3072,2.4182); (4.0189,1.2617,1.6696); (3.6496,1.0249,2.1841); (1.4063,1,1.6759); (1.7695,1.0548, 1.7732); (2.6922,1.2477,1.7457); (3.1261, 2.0082,2.2101); (1.2172,1,1.7298); (2.1479,1.3043,1.9896); (4.7863,1.2058, 2.2182); (5.633,1.7767,2.3631); (1.8918,1,1.7459); (2.6392, 1.107,2.0216); (1.0942,1,2.0522); (4.4297,1.2512,2.2565); (4.3833,3.6815, 2.2078); (1.9222,1.0097,2.0898); (7.9147, 3.8315,2.4972); (3.9636,1.2749,1.9351);

(3.58,1.0199,2.202); (1.6291,1,1.4222); (9.3069,6.0669,2.4608); (1.3206,1,1.549); (2.5398,1,1.6866); (1.0237,1,1.9093); (5.513,1.7048,2.1696); (1.4494,1.0202,2.186); (2.214,1.4617,2.2043); (1.8583,1.0324,2.2307); (2.6043,1.4825,2.0708); (2.5443,1.0496,2.1975); (2.4356,1.0567,2.0849); (6.1421,1.6865,2.4019); (7.443,2.8645,2.4081); (3.3289,1.1963,2.2127); (3.7299,1.2414,2.1591); (2.5093,1.7942,2.1747); (40.298,37.241,2.8295); (3.1873,1.2203,1.9064); (2.0926,1.0178,1.9595); (3.0098,1.0844,1.9168); (3.747,1.7177,1.922); (1.6736, 1.0401,1.9408); (1.0484,1,1.9346); (7.3813,8.0153,2.3418); (2.7578,1.4983, 2.1471); (9.0577,2.0012,2.4568); (1.3034,1,1.7989); (2.907, 1.0923,2.2839); (7.3531,1.315,2.1725); (1.0854,1,2.0323); (3.5334,1.1792, 1.8319); (2.325,1.1434,2.1665); (3.0969,1.3026,1.8871); (7.2238,2.1095,2.2777); (4.1946,1.5703,1.9967); (9.3597,2.296,2.1934); (6.1903,1.1639,2.1712); (1.1509,1,1.7618); (3.2929,1.0368, 2.0977); (3.4032, 1.617,2.1569); (2.1083,1.0174,1.7528); (2.3244,1,1.3998); (17.208,15.893,2.6938); (2.6174,1.7523, 1.8681); (1.3733,1,2.1337); (1.6968,1.0074,1.8211); (1.6724,1.0506,1.8563); (2.1292,1.0248,2.1437); (1.6016, 1.0574,1.9132); (2.5658,1.1937,2.1662); (1.2945,1,1.6996); (2.4844,1.0131,1.6681); (2.2672,1.0082,1.5219); (5.5748,3.9406,1.8788); (1.4325,1,1.5578); (3.5056,3.0217, 1.9848); (2.0043,1.1309,1.9628); (15.729, 11.08,2.5714); (2.6658,1.9992,1.8887); (1.5047,1.0033,1.9641); (4.1788,1.9992,1.3703); (10.383,2.022, 2.3194); (16.279,10.842,2.5824); (1.6427,1.0069,1.9428); (3.1412,1.0745,1.7612); (2.323,1.0117,1.8173); (3.9792,2.173,2.1264); (6.3185,2.9737,1.7781); (9.1926,6.9061,2.1541); (2.4123,1.0432,2.1312); (1.1323,1, 1.9321); (5.8893,1.7449,2.2464); (6.9527,2.8766,2.2108); (1.8834,1.0986,2.134); (5.5742,2.6059, 2.2454); (3.3838,1.0124,1.8559); (3.3317,2.082,2.2072); (2.5455,1.2249,1.8117); (1.2012,1,1.8277); (8.5878, 4.6067, 2.355); (1.6379,1.0055,1.8409); (6.4,7.1725,2.2241); (6.0454,2.8236,2.0595); (2.1808,1.1302, 1.9284); (1.4428,1, 2.0728); (1.4675,1,1.4798); (1.7788,1.0089,1.8672); (3.1904,1.4789,2.2153); (7.9944, 6.2446,2.3473); (2.3983, 1.0598,2.2288); (1.2537,1,1.5056); (2.6879,1.0332,2.1816); (1.2751,1,1.6369); (2.048,1.0017,1.8342); (3.6797,1.2277,2.0372); (2.3209,1.0753,1.615); (5.4859,2.0641,2.4828); (4.2224, 4.9682,2.105); (3.0996,1.0338,1.7005); (1.4714,1,2.2098); (1.3496,1,1.9235); (13.597,11.156,2.4718); (22.311,11.42,2.5936); (4.0097,2.2509,1.9125); (3.334,1.2314,2.2787); (2.5502,1.0734,2.0786); (2.2667,1.0527,1.5966); (1.2647,1,1.7129); (5.242,2.3887,2.3613); (3.5977,1.0246,1.7322); (2.3438,1.0003,1.4745); (3.2758,1.1763,1.7635); (2.8239,2.0063,2.0948); (1.6549,1,1.2424); (2.8302,2.0058, 1.9613); (1.029,1,1.9476); (10.019,1.9877,2.3269); (3.3131, 2.0054,2.0378); (3.5812,1,1.2285); (1.6993,1.0109,2.0132); (7.6446, 1.6096,2.3216); (1.1781,1,1.8123); (2.0668,1,2.0411); (4.4527,1.1356,1.7905); (1.5174,1.021,2.1006); (5.7225,1.2629,1.6944); (1.4918,1,2.116); (2.6043,1.4825,2.0708); (1.909,1.1043,2.2491); (4.2605,1.2093, 2.1889); (2.6047,1.0119,1.9499); (1.1842,1,1.7664); (3.1867,2.0596, 2.3305); (2.2781,1,1.8873); (8.3771, 5.7693,2.4252); (2.2838,1.0311,1.5379); (4.9576,2.0558,2.3063); (2.6418,1.2869,2.1325); (3.1904,3.9945,1.6038); (4.3776,1.5726,2.1133); (2.3516,1.1223,2.0517); (3.3116,1.1289,1.9872); (2.3137,1.0446, 1.6825); (2.837,1.7667,2.0717); (8.7383,7.1337,2.1816); (4.2721,2.5215,2.098); (3.8968,1.434,2.2898); (1.9174,1.0196,1.7804); (9.7279,5.1882,2.4856); (6.2459,2.1042,2.3248); (1.1313,1,2.017); (4.1135,3.1737, 2.2264); (2.5398,1.0305,1.4332); (1.8507,1.006,1.8459); (44.544,47.523,2.8793); (1.5874,1.034,2.0763); (1.634,1,1.1913); (3.8006,2.0309,1.7465); (12.258,11.911,2.2898); (1.5635,1,1.5588); (1.267,1,1.7808); (10.428,1.5721,2.3169); (2.1659,1.0016,1.6855); (2.4093,1.0479,2.1403); (13.911,11.491,2.2504); (1.1486, 1,1.806); (25.796,21.117, 2.7245); (4.432,1.3576,2.0531); (1.8493,1.022,1.789); (4.5145,1.9595,2.1303); (1.158,1,1.6533); (2.6257,1.9992,2.0528); (6.1318,1.6879,2.3539); (1.2012,1, 1.8277); (6.8572,2.6133, 2.3073); (2.5429,1.127,1.8961); (1.2479,1,1.7772); (3.9291,1.1016,2.2667); (3.4424,2.0146, 1.7382); (14.235,5.4966,2.6229); (1.1366,1,1.7392); (6.0809,2.1716,2.0295); (1.1869,1,1.6451); (7.2765,2.0692, 2.3334); (6.7744,1.1155,2.1715); (1.2255,1,1.803); (2.515, 1,1.7961); (1.4877,1,1.5736); (3.5061,1.4363,2.1943); (3.1467,1.2538,2.2241); (3.3322,1.9992,1.4732); (4.3651,2.3742,2.1743); (1.062,1,2.1246); (9.9071, 3.1204, 2.2619); (1.2479,1,1.7772); (5.0209,1.3808,1.9463); (1.6432,1.0077,1.8534); (1.115,1,1.9506); (1.4686,1,1.5425); (5.4926,1.6924,1.7569); (2.7316,1.0111, 2.1258); (11.429,8.0126,2.3309); (8.3239,2.6296, 2.3371); (2.1094,1.7015,1.8391); (14.366,6.9949,2.4326); (2.0313,1.3303,2.17); (5.49,2.0346,2.4629); (8.9543,2.8833,2.3066); (4.4328,1.6622,2.0436); (1.1122,1, 1.9289); (4.2187,4.7277,2.212); (2.5866,1.0336, 1.8744); (1.6497,1,1.8612); (6.2048,2.1546,2.0455); (2.4838,1.0166, 1.8217); (3.4472,1.3401,1.7705); (7.0158,3.7493,1.9173); (1.6354,1.0656,2.0522); (3.2376,1.2317,2.0837); (9.0466,11.514,2.2278); (2.9347, 1,1.7048); (8.1735,3.8233, 2.2447); (11.781,6.3283,2.2585); (2.0062,1,1.9962); (25.754,15.334,2.5838); (2.9205,1.0757,2.1819); (3.0241,1.8849,1.9833); (4.4528,3.1609,2.1455); (2.9347,1, 1.7048); (2.2687, 1.2363,1.9698); (1.7173,1,1.8117); (3.0755,1.3198,2.0249); (1.8273,1.0057,1.8545); (4.4849,2.3766,1.7528); (1.3266,1,1.7406); (3.1852,1.3174, 1.76); (1.0772,1,2.0455); (11.086,2.1077,2.3769); (1.6981, 1,1.7772); (2.1376,1.1109,1.6879); (2.7408,1.4266,1.7512); (1.0899,1,2.0983); (6.0672,1.8825,1.8288); (1.1063, 1,1.8262); (1.0918,1,2.0298); (3.8752,1.3456,1.533); (4.7713,2.4545,2.0547); (2.8479,1.002,1.7546); (5.3542,3.9007,2.3403); (1.0332,1,1.9064); (7.9186,2.615,2.2321); (1.0948,1,1.8259); (1.198,1,1.753); (1.8071, 1.0009,2.0464); (3.5444,1.7315,2.2056); (5.3455, 3.4029,2.2014); (3.3832,2.3049,2.174); (2.9811,1.1624, 2.2222); (2.6176,1.9411,1.8947); (1.7493,1,1.3128); (3.9507,1.5629,1.816); (4.8408,1.9136,2.2582); (1.3455,1,1.6266); (5.7179,5.4978,2.1276); (2.7608,1.195,2.3087); (1.9074,1.1112,1.8704); (6.7633,4.2089, 2.2929); (1.8481,1.007,2.2078); (2.9327,1.0766,2.3073); (4.1817,2.0453,2.1409); (5.7006,2.2621,1.4722); (3.6496,1.0249,2.1841); (3.6795,1.3631,2.1825); (16.068,10.23,2.5635); (2.102,1,1.2431); (2.5712, 1,1.4863); (7.4025,4.3854,2.3687); (3.4125,1.2509,2.0575); (1.1639,1, 1.7948); (1.7344,1,1.7753); (5.6188, 3.0905,2.1467); (3.5406,1.4508,2.1584); (1.4804,1,1.6027); (4.6055,1.3871, 1.8586); (1.1313,1,2.017); (2.0256,1,1.3246); (1.1128,1,1.7534); (3.0827,1.7047,1.9509); (3.7682,1.2901, 2.2307); (1.4926,1,1.6039); (2.3006,1.0406,1.8623); (3.425, 1.1941,2.1303); (5.9377,1.277,1.8534); (30.857,27.911,2.7529); (1.4325, 1.0049,1.9451); (2.216,1.0191,2.0797); (1.0724,1,1.9262); (3.7246,1.0812,1.3646); (3.1115,2.1406,2.1734); (1.1166,1, 1.7869); (3.4185,1.0491,1.9011); (2.5851,1.7782,2.2763); (4.704,3.0547,2.1258); (1.2346, 1,1.6432); (12.465,4.4196, 2.4762); (1.9473,1.0399,1.8386); (2.9405,1.6174,1.7563); (6.7638,2.143,2.4058); (3.5409,1.2465,2.0063); (1.1636,1,1.7057); (1.5714,1,1.4282); (2.5547,1.0488,1.8438); (1.2356,1,1.7139); (3.5928,3.0602, 2.2434); (1.9093,1.0089,1.7901); (2.9143,1.1118,1.852); (1.6679,1.0252,1.97); (1.6651, 1,1.4623); (5.838,1.7565,1.7954); (3.0031,1.9992,1.7424); (6.0025,5.0524,2.1982); (4.4109,2.6704, 2.1921); (5.6095, 2.7956,2.3436); (3.5643,1.1608,1.8628); (3.3721,2.4988,2.181); (20.179,4.5197,2.5971); (5.8659,1.84,2.2964); (1.8901,1.0782,1.883); (10.178,4.1908,2.45); (1.2489,1,1.7544); (1.9598,1,1.3717); (2.6002,1.1285,2.2294); (8.5274,2.3133,2.2255); (5.5305,4.9552,2.2968); (2.2201,1.0301,1.6923); (4.979,2.0763,1.8949); (6.1032,5.8457,2.1297); (1.3369,1,1.7451); (2.0642,1.0569,1.7294); (9.5201,7.8543, 2.5051); (3.9615,1.0225,2.2017); (2.4159,1.1345,1.9028); (3.7522,1.3008,2.0276); (5.7343,2.1411,2.2518); (23.117,17.808,2.5514); (1.5246,1.003,1.9346); (2.6647,1.3601,1.8504); (2.779,1.2637,2.0956); (4.5299, 2.1871,2.0369); (2.0531,1.0112,1.9112); (1.9185,1.0884,1.8468); (1.723,1.0016,1.8132); (3.6496,1.0249,2.1841); (1.4931,1.0418,2.0195); (2.0669,1.004,1.8667); (1.6284,1,1.3974); (1.6021,1,1.9391); (4.1993, 1.9339,2.1367); (2.0285,1.1884, 1.8954); (1.8765,1,1.3979); (3.509,1.7184,1.7993); (2.4598, 1.0109, 2.2687); (8.1014,2.7455,2.3223); (2.0333,1.0538,1.9631); (5.6486,1.6573,2.2043); (2.4212,1.0011,2.0694); (2.9281,1.2743,2.0235); (2.2561,2.146,2.0052); (1.0661,1,1.8559); (1.9956,1,1.6978); (6.9971,3.0632, 2.3829); (1.8421,1.1833, 1.9428); (4.0821,1.0885,2.1876); (1.0415,1,1.9654); (5.2685,1.2816,2.0114); (17.874,5.4079,2.6097); (1.6259,1.0177,1.9476); (3.181,1.1508,2.2739); (6.1083,1.2844,2.3041); (5.9518,3.2734,2.288); (8.4629,3.5524,2.2114); (13.166,6.3207,2.4897); (6.7946,2.1253,2.3191); (2.9057,1,1.7424); (6.6135,5.5167, 1.8637); (6.0366,4.5247,2.2189); (3.4349,1.2235,1.8847); (5.6557,1.6238,2.2684); (4.2998, 2.191,2.3385); (4.5982,2.0536,1.8178); (2.3562,1.0361,2.187); (3.237,1.2049,2.1089); (13.499,4.7103, 2.3309); (4.8684,1.5116,2.2954); (1.388,1,2.1077); (6.147,6.1203,1.8097); (1.3171,1,1.6398); (1.9505, 1.0421, 2.0855); (1.0386,1,2.091); (4.5599,1.2379,2.0489); (3.8831, 1.5281,2.1978); (1.185,1,1.7833); (2.7812, 1.2443,1.8556); (4.4849,2.3766,1.7528); (3.321,2.0821,2.2777); (1.1225,1,1.9649); (1.4447,1,1.6162); (16.315,5.1717,2.4236); (9.79,2.4595,2.2311); (12.174,9.3961,2.1609); (2.4281,1.0311,1.4052); (1.4918, 1,2.116); (1.1529,1,1.6362); (2.2367,1.055,2.1184); (9.3252,4.5128,1.8273); (3.485,3.6131,2.246); (3.4005,1.1837,2.1443); (1.47,1,1.6415); (1.2608,1,1.7261); (10.919,5.3137,2.5295); (1.5255,1.0152,1.9969); (1.2945,1, 1.6996); (4.7239,1.194,1.8871); (3.1354,2.3309,2.023); (3.2889,1.2053,2.1772); (2.8002,1.4993, 1.3517); (3.1015, 1.0485,1.6652); (4.1793,1.8862,2.0939); (1.4745,1,2.1337); (1.7892,1,1.3438); (1.6681, 1.014,1.9433); (5.3825,3.6477, 2.2541); (4.5504,1.9992,1.4705); (3.9051,3.0416,2.0433); (2.6648,1.0421,1.9814); (1.908,1.1072,1.9421); (1.6757,1.0445,2.0629); (1.3903,1,1.6652); (4.9946,2.435,1.976); (5.6354,1.5243,2.2248); (8.6497,11.566,2.3338); (1.6651,1,1.4623); (3.3701,1.2604, 2.1628); (6.0777,3.6526, 2.3928); (3.4235,1.7808,2.202); (8.451,2.7797,2.5223); (2.9261,1.0024,1.5483); (2.6664,1,1.2798); (1.0936,1,2.0655); (3.229,1.2641,2.105);

(1.71,1.0086,1.8545); (2.6296,3.9945,1.776); (3.315,1.7913,2.1606); (4.9739,1.5645,1.4445); (2.4965,1.0045,1.4616); (1.0283,1,2.0875); (2.2474,1.2429, 2.1306); (7.0479, 4.5734,2.3698); (3.37,1.1512,2.1027); (3.8077,1.2541,2.146 1); (1.5511,1,1.9426); (1.4305,1,1.4674); (3.2979,1.2692,2.2248); (11.313,2.8997, 2.4504); (4.1388,1.5814,2.2297); (26.056,11.001,2.6804); (2.1412, 1.1466,1.7402); (1.9621,1,1.4295); (4.476,2.3409, 2.4318); (2.0421,1.2354,2.1934); (10.605,2.6777,2.4742); (8.9128,4.4931,2.0652); (3.104,2.0009,1.678); (8.0163,1.3877,2.313); (3.1785,1.9992,1.7503); (2.9172, 2.0046,1.9724); (1.0975,1,2.0542); (5.0353,4.7006,1.8925); (1.8741,1.0541,1.8362); (1.9775,1.0129, 2.1319); (2.9328, 1.0748,1.8913); (4.6892,1.4936,2.3141); (2.0986,1.0067,1.9341); (2.7088,1.0493,1.7787); (2.198,1.1936,1.6729); (2.3905,1.082,2.1358); (3.7674,2.0051,2.076); (2.8665,2.0079,2.1425); (4.1873, 1.8145,2.0009); (1.1335,1,2.1322); (15.431,5.1429,2.5754); (7.4325,2.2084,2.5001); (6.0451,2.3778,1.9501); (8.181,2.8041,2.3694); (4.4474,1.6069,1.9641); (7.6606,4.955,2.4754); (2.9621,1.3937,1.7651); (10.45,8.4386,2.2971); (2.5042,1.7546,2.3216); (3.1793,3.0999,1.9338); (22.918,17.166,2.6563); (2.6024, 1.0478,1.7166); (2.4036,1.0201,1.7372); (5.1116,2.5704,2.4389); (4.5963,2.0356,1.4512); (1.7817,1, 1.5107); (2.756,1.9992,1.8536); (1.2527,1,1.6373); (7.4728, 4.6353,2.2354); (8.7902,5.0318,2.1157); (8.6423, 5.1754,1.7182); (5.933,2.9202,2.2915); (1.2006,1,1.8835); (1.8422,1.048,1.7793); (2.7683,2.1262,2.203); (3.1466,1.0449,2.2284); (3.3293,2.0862,1.7316); (3.9522,1.2191,2.1486); (1.7465,1.0012,1.773); (21.403, 15.189,2.5785); (6.7187,2.6128,1.8973); (10.366,2.4938,2.3777); (3.5785,1.4767,2.2732); (2.3357,1.1181,2.0584); (4.7268,1.9992,1.3015); (45.803,46.655,2.9603); (6.7568,2.9258,1.8812); (6.609,2.5072,2.4259); (8.6117,1.9145,2.3155); (1.5439,1.0012,1.9134); (2.6244,1.0463,2.1325); (2.9543,1.9992,1.7376); (6.5738,3.5171,2.2238); (3.5846,1.8251,2.1195); (2.5694,1.0457,1.7952); (1.4481,1, 2.0001); (9.2967,3.3369,2.2891); (1.7413,1.0096,1.8488); (1.5258,1,1.7123); (3.5013,1.419,2.0378); (1.3641,1,2.1068); (2.0915, 1.0223,1.9213); (4.3858,1.585, 2.1911); (1.1684,1,1.7846); (3.4424,1.8758,1.8518); (1.642, 1.0006,1.7429); (5.0015,1.8533,2.0757); (1.4293,1.0003,2.1753); (3.7426,1.0736,2.307); (11.721,3.7859,2.4461); (4.1179,1.0739,1.7972); (5.2685,2.4398,2.3363); (1.2934,1,1.6511); (1.185,1,1.8262); (1.5484,1.0025,1.9235); (2.8911,1.1471,2.3867); (1.5209,1.0146,2.0411); (4.3947,1.346,2.2301); (2.7089,1.3776,1.9768); (4.7719,2.0219,1.5528); (2.9199,1,1.4703); (7.3012,4.4716, 2.0768); (2.0323,1,1.6681); (1.0873,1,1.7536); (5.0038,3.3011,2.2307); (9.2197,5.0117,2.2811); (1.6062,1, 1.599); (4.5201,2.999,2.0706); (4.076,2.1527, 1.7514); (1.8012,1,1.6403); (14.123,8.4814,2.1972); (2.5686,1.1222, 1.903); (3.3965,1.9992,1.5562); (6.9663, 3.5209,2.265); (4.4321,1.2441,1.9096); (1.1684,1,1.7846); (2.4056,1,1.212); (8.2224,4.4579,2.2982); (4.3515,1.1355,1.5601); (1.2626,1,1.7697); (2.916,2.2599,2.0892); (1.5212,1,2.0167); (1.3991,1,1.529); (5.2099,1.246,2.3447); (1.5809,1,1.4534); (3.4014,1.07,2.0618); (1.2826,1,1.7818); (2.7912,1.9992,2.0663); (31.287,29.416,2.8804); (1.3765,1, 1.6098); (1.1212,1,1.8284); (1.9775,1.0129,2.1319); (4.1745,1.6286, 2.2179); (4.6056,2.288,2.2884); (2.2667,1, 1.5718); (5.1753,3.0147,2.2407); (2.0422,1.1129,1.7382); (1.1366,1,1.7392); (1.2541,1,1.7211);

(2.8816,1.0681,2.1291); (1.6466,1.0128,1.7306); (2.562,1.0486,1.9724); (14.7,5.2151,2.3837); (2.4617,1.1085,2.0991); (4.0471,1.1856,2.152); (1.2319,1, 1.6542); (2.3418,1.0628, 1.876); (4.672,1.6564,2.3502); (6.379,1.716,2.4042); (3.421,1.4621,2.214); (4.9404, 1.6688,2.3993); (1.5225,1.0063,2.0146); (2.2897,1.0009,1.7823); (2.2837,1.0606,2.1358); (2.1004,1.0208,2.1486); (1.0586,1, 1.7816); (2.46,1.0033,2.2059); (1.2766,1,1.6226); (2.3841, 1.0165,2.1056); (2.9898, 2.531,2.1352); (3.5115,1.104,1.6043); (1.9566,1.0076,2.0806); (2.3315,1.0467,2.1918); (3.7531,2.0401, 1.9893); (2.563,1.0234,2.0991); (2.3493,1.0758,1.8025); (3.5299,1.7097,1.6986); (6.5014,3.5724,2.0178); (15.382,6.9569,2.6335); (1.2742,1,1.5724); (16.709,7.9999, 2.6642); (2.7444,1,1.6661); (11.816,4.2743, 2.2992); (4.585, 5.0225,2.230 1); (13.585,5.5789,2.458); (16.465,7.8613,2.3003); (3.9742,1.9304,2.2694); (2.7591,1.0031,1.5855); (13.814,7.9858,2.4385); (3.1525,1.9992,1.589); (1.1664,1,1.8384); (5.9544, 1.3408, 1.9267); (5.629,1.6711,2.355); (3.0533,1.2612,1.7463); (1.974,1.3549,2.2407); (2.2039,1.0117,1.5469); (1.8255,1.1662,2.1612); (5.0858,2.2203,2.2514); (13.185,3.3483,1.9775); (1.687,1.0609,2.1163); (4.4464,2.3913,2.2344); (1.2019,1,1.7396); (1.8291,1.1825, 1.9675); (5.6626,2.5579,2.313); (1.3871,1,1.7219); (2.2939, 1.5213,2.0881); (1.1867,1,1.8053); (15.022,6.0286,2.4429); (3.5046,2.0108,1.7991); (10.349, 6.2855,2.452); (1.1626,1, 1.7594); (2.6677,1,1); (1.3266,1,1.7406); (1.1247,1,1.836); (4.6308,1.3386,2.2968); (1.115,1,1.9506); (5.0755,1.4613,1.5006); (1.5494,1.0024,1.9721); (1.7157,1.0318,1.8377); (2.9284, 1.6094,1.8138); (2.5492, 1.0355,1.9796); (3.2297,1.0001,1.4774); (6.2614,2.5551,2.2189); (2.4627,1.0347, 2.2176); (2.0182, 1.0026,1.8591); (13.025,3.6169,2.4584); (2.0697,1.2663,1.8866); (4.4103,3.6875,1.7542); (4.5627,1.3171,2.0157); (1.365,1,1.6714); (1.8832,1.0114,2.1112); (1.108,1,1.8628); (10.306,9.9904, 2.3327); (3.2803,1.5398,2.3425); (19.231,15.037,2.3066); (1.3975,1,1.6504); (5.7236,4.7679,2.3447); (5.2099,1.246,2.3447); (3.2758,1.1763,1.7635); (2.0739,1.0196,2.0878); (3.243,1.0001,1.3464); (1.1183, 1,1.6637); (6.2262,1.5188,2.3784); (7.6596,4.8033,2.3739); (1.9262,1.0191,1.7829); (32.462,21.171,2.6704); (1.2346,1, 1.6432); (14.539,3.8909,2.4588); (5.3195,1.523,2.0055); (5.1065,1.2884,2.3572); (7.9066, 5.0651,2.1816); (3.7127, 1.1214,2.268); (3.0295,1.4993,1.4513); (1.6377,1,1.8579); (1.8803,1,1.392); (3.554,2.0019,1.5139); (5.6257,2.1726,2.0124); (2.4056,1,1.212); (4.5024,2.9919,2.2347); (5.0079,1.5246, 2.3484); (2.645,1.6283,2.1778); (1.6296,1.0121,1.961); (5.4872,1.0917,1.8956); (4.7031,2.6926,2.1835); (2.5973,1.2037,1.4178); (2.6648,1.0421,1.9814); (2.9186,1.0008,1.8112); (9.9378,6.2505,2.4464); (7.0717, 3.8945,2.3349); (3.385,1.2072,2.2595); (1.0712,1,2.1151); (2.3642,1.0449,2.0615); (5.6083,2.6334,2.1325); (39.493,31.203,2.8194); (1.3166,1,1.69); (46.299,36.165,2.7809); (4.6401,1.2976,2.1693); (3.3428, 2.0221,2.1959); (1.7758,1.0117,1.9062); (2.3539,1.0003,1.6641); (1.2484,1,1.8438); (28.483,21.546, 2.6751); (3.8851,1.0501,1.8328); (1.3549,1,1.6668); (1.8106,1.036,1.8676); (3.0231,1.0132,1.1969); (3.2608, 1.0003,1.8347); (1.8187,1,1.5265); (1.4802,1,0.0125,2.1331); (1.3979,1.0013,2.0657); (7.8671,3.0571,2.287); (2.329,1.1906,1.827); (3.5314,2.2157,1.7972); (2.3079,1.2401,1.8447); (1.3484,1,1.5452); (2.7147,1.2696, 2.3059); (3.6006,1.088,1.9983); (1.4636,1,1.6027); (4.2678, 2.5118,1.958); (2.3819,1.0019,2.1529); (2.0487,1,1.7835); (1.2214,1,1.7188); (2.6623,1.1154,2.1756); (5.7962,1.6445, 2.0464); (1.8029,1.0003,2.1994); (1.3171,1,1.6398); (8.6269,1.4522,2.3531); (1.5688,1.0068,1.9181); (8.4075,1.6577,2.3517); (6.0587, 3.6758,2.0436); (13.081, 9.2426,2.5596); (3.6496,1.0249,2.1841); (4.6101,2.2946,2.3735); (4.4054,1.8208,2.3223); (2.0353,1.6042,1.8095); (1.1036,1,1.9436); (3.0371,1.0551, 2.2575); (3.0067,1.0856,1.9983); (2.1959,1.117,2.14); (3.0063,1.2834,2.288); (1.2006,1,1.8835); (3.5091,1.226,1.9856); (3.8147,1.5037, 2.2404); (2.7444,1, 1.6661); (11.173,5.5676,2.521); (2.8353,1.1343,1.9086); (1.0111,1,1.958); (1.8599,1.0011,2.2069); (7.181,3.3873,2.3119); (8.139,2.5175,2.2387); (11.532,6.273,2.1489); (1.8071,1.0009,2.0464); (1.9594,1.0222,1.9608); (3.5982,1.5567,1.9466); (6.1403,2.9982,1.8513); (6.0125,2.5546,2.3631); (8.0061,2.7333,2.2811); (2.2575,1.1264,2.0222); (4.7648,1.8516,1.8413); (6.5794,2.5129,2.2954); (1.3238, 1,1.5916); (3.0591,1.2468,1.74); (8.4393,4.2172,2.0956); (2.0353,1.6042,1.8095); (1.1326,1,1.8461); (24.479,13.553, 2.6647); (1.3898,1,1.6224); (3.3405,2.02,1.8568); (4.1948, 5.6048,2.0298); (2.4445,1.2899, 2.148); (1.5258,1,1.7123); (2.48,2.1267,1.9237); (3.0141,1.2501,1.816); (2.7176,1.0154,1.7487); (2.3529, 1.0927,1.7606); (1.2302,1, 1.8041); (1.4374,1.0185,2.0309); (14.627,4.4815,2.4244); (11.488,5.5326,2.6088); (4.3238,2.1148,2.064); (1.6816,1.0306,1.9641); (5.2869,1.6521,1.4901); (3.3554,1.1951,1.7503); (3.6202,2.0078,2.1765); (2.713,1.2021,1.7802); (6.3146,3.0908,2.216); (1.6796,1.0318,2.1328); (6.2551,2.8553,2.422); (3.8393,2.1827,2.0007); (1.1526,1,1.6921); (1.2917,1,1.6915); (2.3068,1.0671,2.0863); (3.5291, 1.2608, 1.9603); (3.3002,2.319,2.1972); (3.1266,1.2625,2.1376); (8.6806,3.7515,2.1991); (6.7673,2.806,2.4042); (2.2946,1.0361,1.4983); (2.278,1.0333,1.6058); (4.0957,1.6927,1.811); (1.7235,1.0525,2.0375); (1.1966,1,1.7884); (3.1703,1.0661,2.2049); (2.1535,1.0124, 2.0691); (1.4588,1,1.412); (1.3099,1,1.6314); (1.2489,1,1.7544); (1.3878,1,1.735); (7.7746,3.6113,2.3546); (1.1321,1,1.9499); (2.0735,1.0842, 2.0159); (4.0042,1.5293,1.5789); (1.5226,1,1.957); (7.6654, 3.53,2.0595); (3.5741,1.7709,2.1734); (2.2087,1, 1.7119); (7.3399,3.4652,2.4166); (2.103,1.0086,1.7336); (8.0386,2.634,2.5151); (3.7536,1.9992,1.5721); (2.7591,1.2753,2.05); (14.579,9.8703,2.6138); (1.0167,1,1.9565); (6.5493,4.1002,2.1603); (2.4334,1.3311, 1.557); (1.9413,1.0172,1.9888); (16.044,10.729,2.5618); (3.2475,4.5342,2.235); (3.2543,2.0052,1.7901); (6.0475,2.342,1.4765); (10.568,4.7579,2.3792); (1.1457,1,1.7457); (15.881,11.272,2.5505); (2.1857,1.0815, 1.9428); (3.1535,1.0428,2.2404); (1.8287,1,1.9481); (8.9362,5.4706,2.4035); (4.7114,1.6156,2.3126); (1.3099,1, 1.6314); (9.8126,2.8813,2.4984); (8.5353,3.9028,2.3765); (1.2945,1,1.6996); (3.3784,1.0092, 1.8064); (6.2723,2.5051, 2.3262); (2.9177,1.3043,2.2407); (1.0322,1,1.9962); (2.4883,1.0657,1.8493); (1.079,1,1.7069); (4.1242,1.1746,2.3066); (3.1917,1.2192,1.8935); (58.463,88.935,2.9122); (5.7608,3.2743, 1.7914); (4.7495, 1.1039,1.5398); (1.6508,1.0586,2.0954); (1.7518,1,2.1784); (1.3538,1,1.8651); (1.374, 1,1.6819); (4.2773,2.3523,2.148); (3.7821,1.1338,2.0052); (1.101,1,1.6975); (1.3034,1,1.7989); (4.3521, 1.4005,2.2437); (4.0155,1.0638,2.2756); (2.368,1.135,1.8017); (2.6225,1.0191,1.784);

(1.0918,1,2.0298); (2.1037,1.0019,1.5992); (4.3551,1.7299, 1.9496); (2.5133,1.2571,2.0154); (4.1436,3.0594,1.9532); (1.9413, 1,1.7288); (3.0405,2.9976,2.0924); (2.8432,1.3447, 2.0309); (7.0903,4.2616,1.8306); (1.4818,1,1.4894); (1.3033,1,1.755); (4.7464,1.6671,2.2825); (6.376,1.6303,2.2585); (1.0899,1,2.0983); (1.5226,1,1.957); (1.2906,1,1.6933); (1.8017,1,1.6319); (3.4659,1.4257,2.165); (5.2547,2.7244,2.1437); (8.3371,6.17,2.2873); (3.6851,1.5661,2.1765); (6.1031,2.6431,2.2599); (1.8517,1.0069,1.9967); (6.4718,1.0936,2.1391); (2.7885,1.0982,1.7716); (19.858,7.4654,2.594); (1.2321,1,1.7188); (1.9566,1.0076,2.0806); (2.3099,1.0681, 1.7818); (2.3903, 1.0544,2.0517); (1.1511,1,1.8797); (8.8973,2.6562,2.2964); (4.6163,1.151,1.534); (2.2511,1.2662,1.9552); (4.4431,1.2709,2.0369); (1.8073,1.0016,1.5133); (2.9284,1.0457,2.2846); (6.1928, 3.5268,2.2735); (2.3053, 1.1446,1.8612); (2.3591,1.0486,2.0001); (1.1069,1,1.836); (1.8571,1,1.5035); (5.8287,2.7983,1.7082); (2.5588,1.1597, 1.7952); (9.3139,6.3325,2.4275); (8.6995,7.1534,2.4877); (3.1256, 2.004,1.7404); (1.1247,1,1.836); (3.6309,1.3061,2.3158); (2.0484,1.0034,1.7635); (7.2108,5.9999,2.5206); (5.6211,2.9979,1.687); (5.2267,2.2311,2.392); (2.2559,1.0637,1.6582); (1.5974,1.0093,1.9651); (1.3455, 1,1.6266); (4.2769,1.1673, 2.3724); (5.0103,1.7704,1.9309); (1.9577,1,1.7487); (3.0464,3.9945,1.7418); (3.1894,2.7029,1.9122); (4.6727,2.2373,2.194); (2.713,1.2021,1.7802); (5.19,2.2204,2.2866); (3.2122, 1.5911,2.0916); (8.9043,2.5346,1.9962); (2.551,1.0357,1.777); (3.2408,1.1689,2.0257); (1.2934,1,1.6511); (1.198,1,1.753); (4.4624,1.9992,1.4009); (1.6209,1.0776,2.1584); (3.2616,1.3987,2.2248); (5.3209,1.9657, 2.3498); (15.381, 7.1406,2.2255); (3.2385,2.2197,2.1325); (3.5314,1.0191,2.202); (2.6961,1.1775,2.2324); (1.3484,1,1.5452); (4.1377,1.7455,2.1628); (1.1664,1,1.8384); (2.4759,1.0342,1.9453); (3.0716,1.3475, 2.2394); (1.1486,1,1.806); (2.3457,1.1041,1.956); (2.1758, 1,1.6959); (3.5275,1.0456,1.8711); (5.6884, 2.4599,2.2763); (4.7457,2.1567,2.2377); (5.4312,5.2033,2.1391);

Part II: IP Values of Sinomenine-Related Genes

| Gene | IP value | NodeRank | Betweenness | Closeness |
|---|---|---|---|---|
| 581 | 6.1834 | 6.5855 | 1.7778 | 2.2853 |
| 596 | 18.265 | 15.978 | 9.3801 | 2.5303 |
| 6347 | 6.3687 | 6.2869 | 2.4204 | 1.9626 |
| 6348 | 5.3322 | 4.7031 | 2.6926 | 2.1835 |
| 6352 | 10.809 | 7.3813 | 8.0153 | 2.3418 |
| 958 | 5.7661 | 5.7343 | 2.1411 | 2.2518 |
| 941 | 2.1418 | 1.9577 | 1 | 1.7487 |
| 942 | 2.1418 | 1.9577 | 1 | 1.7487 |
| 1027 | 12.133 | 11.173 | 5.5676 | 2.521 |
| 1278 | 11.793 | 11.816 | 4.2743 | 2.2992 |
| 9170 | 1.6419 | 1.3043 | 1 | 1.6992 |
| 1906 | 4.2158 | 4.1058 | 1.6685 | 1.9448 |
| 2258 | 4.0385 | 4.2605 | 1.2093 | 2.1889 |
| 2335 | 33.203 | 24.564 | 22.378 | 2.541 |
| 3383 | 3.9573 | 3.883 | 1.5318 | 2.2127 |
| 8519 | 1.9824 | 1.7413 | 1.0096 | 1.8488 |
| 3596 | 1.91 | 1.6399 | 1.0176 | 1.7724 |
| 3553 | 5.0708 | 4.6755 | 2.3195 | 2.2548 |
| 3569 | 2.0616 | 1.8385 | 1.0171 | 2.0677 |
| 3576 | 7.1515 | 5.8846 | 4.1141 | 2.2384 |
| 3714 | 2.2781 | 2.1347 | 1.0015 | 1.7633 |
| 4322 | 4.8742 | 4.5299 | 2.1871 | 2.0369 |
| 4792 | 13.31 | 11.538 | 6.961 | 2.5457 |
| 5228 | 5.7783 | 6.1318 | 1.6879 | 2.3539 |
| 5743 | 14.065 | 8.6497 | 11.566 | 2.3338 |

| Gene | IP value | NodeRank | Betweenness | Closeness |
|---|---|---|---|---|
| 7040 | 17.191 | 13.854 | 10.236 | 2.4697 |
| 7124 | 7.5393 | 7.443 | 2.8645 | 2.4081 |
| 7133 | 4.281 | 4.1738 | 1.689 | 2.2444 |
| 7157 | 102 | 58.463 | 88.935 | 2.9122 |
| 7412 | 8.2158 | 7.461 | 3.8938 | 2.1731 |
| 7422 | 10.992 | 9.8995 | 5.3072 | 2.4182 |

Part III: IP Values of Matrine-Related Genes

| Gene | IP value | NodeRank | Betweenness | Closeness |
|---|---|---|---|---|
| 7356 | 1.4644 | 1.0724 | 1 | 1.9262 |
| 7157 | 102 | 58.463 | 88.935 | 2.9122 |
| 581 | 6.1834 | 6.5855 | 1.7778 | 2.2853 |
| 355 | 9.0518 | 7.6606 | 4.955 | 2.4754 |
| 4893 | 16.583 | 15.486 | 7.3526 | 2.6097 |
| 604 | 5.4139 | 5.8041 | 1.5112 | 2.3273 |
| 3265 | 24.805 | 21.456 | 13.027 | 2.6747 |
| 1026 | 11.776 | 10.919 | 5.3137 | 2.5295 |
| 1032 | 2.9654 | 3.0231 | 1.0132 | 2.1969 |
| 596 | 18.265 | 15.978 | 9.3801 | 2.5303 |
| 567 | 8.4655 | 7.3012 | 4.4716 | 2.0768 |
| 595 | 16.668 | 17.066 | 5.6075 | 2.5557 |
| 4609 | 17.158 | 17.874 | 5.4079 | 2.6097 |
| 5111 | 17.66 | 16.465 | 7.8613 | 2.3003 |
| 3725 | 35.049 | 29.09 | 19.867 | 2.6953 |
| 891 | 7.8855 | 8.0061 | 2.7333 | 2.2811 |
| 7015 | 5.2026 | 4.7123 | 2.4805 | 2.34 |
| 1019 | 14.143 | 13.166 | 6.3207 | 2.4897 |
| 5743 | 14.065 | 8.6497 | 11.566 | 2.3338 |
| 6774 | 39.944 | 29.049 | 27.518 | 2.8158 |
| 6777 | 13.096 | 13.48 | 4.3218 | 2.6266 |
| 4089 | 37.634 | 29.616 | 23.256 | 2.729 |
| 4314 | 6.339 | 6.2773 | 2.3856 | 2.1578 |
| 836 | 40.873 | 28.304 | 29.846 | 2.7015 |
| 1027 | 12.133 | 11.173 | 5.5676 | 2.521 |
| 947 | 1.6313 | 1.2906 | 1 | 1.6933 |
| 3674 | 12.773 | 12.104 | 5.4543 | 2.4275 |
| 5925 | 35.666 | 28.483 | 21.546 | 2.6751 |
| 1029 | 6.8854 | 7.2238 | 2.1095 | 2.2777 |
| 2526 | 8.6439 | 6.147 | 6.1203 | 1.8097 |
| 3684 | 8.7155 | 8.1735 | 3.8233 | 2.2447 |
| 4830 | 12.863 | 11.532 | 6.273 | 2.1489 |
| 7076 | 2.6601 | 2.5605 | 1.0888 | 1.9433 |
| 7408 | 9.4162 | 8.7928 | 4.1756 | 2.1575 |
| 56259 | 1.4583 | 1.0644 | 1 | 1.7306 |
| 174 | 1.4808 | 1.0939 | 1 | 1.8322 |
| 945 | 1.9842 | 1.7518 | 1 | 2.1784 |
| 7040 | 17.191 | 13.854 | 10.236 | 2.4697 |
| 1277 | 13.361 | 13.499 | 4.7103 | 2.3309 |
| 59 | 5.7242 | 4.3833 | 3.6815 | 2.2078 |
| 960 | 17.682 | 14.131 | 10.669 | 2.4803 |
| 7422 | 10.992 | 9.8995 | 5.3072 | 2.4182 |
| 2258 | 4.0385 | 4.2605 | 1.2093 | 2.1889 |
| 7124 | 7.5393 | 7.443 | 2.8645 | 2.4081 |
| 3569 | 2.0616 | 1.8385 | 1.0171 | 2.0677 |
| 1956 | 54.812 | 40.298 | 37.241 | 2.8295 |
| 1281 | 7.5153 | 8.3156 | 1.7904 | 2.2447 |
| 1285 | 5.6574 | 5.8105 | 1.8817 | 2.1285 |
| 4313 | 17.966 | 16.406 | 8.4075 | 2.3031 |
| 2335 | 33.203 | 24.564 | 22.378 | 2.541 |
| 4035 | 26.782 | 18.001 | 20.205 | 2.5557 |
| 3383 | 3.9573 | 3.883 | 1.5318 | 2.2127 |

Part IV: IP Values of Honokiol-Related Genes

| Gene | IP value | NodeRank | Betweenness | Closeness |
|---|---|---|---|---|
| 7157 | 102 | 58.463 | 88.935 | 2.9122 |
| 7124 | 7.5393 | 7.443 | 2.8645 | 2.4081 |
| 3586 | 1.5605 | 1.198 | 1 | 1.753 |

-continued

| Gene | IP value | NodeRank | Betweenness | Closeness |
|------|----------|----------|-------------|-----------|
| 598 | 13.987 | 13.585 | 5.5789 | 2.458 |
| 836 | 40.873 | 28.304 | 29.846 | 2.7015 |
| 6647 | 5.6279 | 5.0143 | 2.7821 | 2.1921 |
| 5443 | 3.0752 | 2.5093 | 1.7942 | 2.1747 |
| 581 | 6.1834 | 6.5855 | 1.7778 | 2.2853 |
| 596 | 18.265 | 15.978 | 9.3801 | 2.5303 |
| 796 | 3.1253 | 3.243 | 1.0001 | 1.3464 |
| 6750 | 3.2638 | 3.2758 | 1.1763 | 1.7635 |
| 4842 | 7.5971 | 6.9663 | 3.5209 | 2.265 |
| 3553 | 5.0708 | 4.6755 | 2.3195 | 2.2548 |
| 4353 | 3.1482 | 3.0533 | 1.2612 | 1.7463 |
| 5743 | 14.065 | 8.6497 | 11.566 | 2.3338 |
| 3791 | 15.49 | 15.469 | 5.6757 | 2.5692 |
| 4318 | 16.366 | 15.381 | 7.1406 | 2.2255 |
| 4843 | 6.6256 | 5.8787 | 3.3044 | 2.2825 |

Part V: IP Values of Luteolin-Related Genes

| Gene | IP value | NodeRank | Betweenness | Closeness |
|------|----------|----------|-------------|-----------|
| 207 | 41.581 | 30.857 | 27.911 | 2.7529 |
| 367 | 45.012 | 29.003 | 35.443 | 2.8493 |
| 581 | 6.1834 | 6.5855 | 1.7778 | 2.2853 |
| 596 | 18.265 | 15.978 | 9.3801 | 2.5303 |
| 598 | 13.987 | 13.585 | 5.5789 | 2.458 |
| 836 | 40.873 | 28.304 | 29.846 | 2.7015 |
| 841 | 17.184 | 15.391 | 8.3992 | 2.4836 |
| 891 | 7.8855 | 8.0061 | 2.7333 | 2.2811 |
| 595 | 16.668 | 17.066 | 5.6075 | 2.5557 |
| 958 | 5.7661 | 5.7343 | 2.1411 | 2.2518 |
| 1020 | 11.262 | 8.6995 | 7.1534 | 2.4877 |
| 1026 | 11.776 | 10.919 | 5.3137 | 2.5295 |
| 1576 | 4.8152 | 4.8053 | 1.7683 | 1.8434 |
| 1906 | 4.2158 | 4.1058 | 1.6685 | 1.9448 |
| 1956 | 54.812 | 40.298 | 37.241 | 2.8295 |
| 355 | 9.0518 | 7.6606 | 4.955 | 2.4754 |
| 2353 | 16.587 | 16.151 | 6.5691 | 2.5419 |
| 2308 | 7.0002 | 5.8731 | 3.8929 | 2.4881 |
| 2309 | 4.8637 | 5.1355 | 1.4512 | 2.4042 |
| 3480 | 28.588 | 22.918 | 17.166 | 2.6563 |
| 3596 | 1.91 | 1.6399 | 1.0176 | 1.7724 |
| 3565 | 1.552 | 1.1869 | 1 | 1.6451 |
| 3569 | 2.0616 | 1.8385 | 1.0171 | 2.0677 |
| 3576 | 7.1515 | 5.8846 | 4.1141 | 2.2384 |
| 3725 | 35.049 | 29.09 | 19.867 | 2.6953 |
| 5594 | 65.085 | 45.803 | 46.655 | 2.9603 |
| 1432 | 28.895 | 23.829 | 16.561 | 2.6671 |
| 5599 | 25.144 | 21.539 | 13.456 | 2.7049 |
| 4792 | 13.31 | 11.538 | 6.961 | 2.5457 |
| 4843 | 6.6256 | 5.8787 | 3.3044 | 2.2825 |
| 142 | 8.5803 | 7.8752 | 3.9678 | 2.3173 |
| 5335 | 26.35 | 24.989 | 11.23 | 2.5846 |
| 9536 | 7.8641 | 6.069 | 5.0018 | 1.8073 |
| 5743 | 14.065 | 8.6497 | 11.566 | 2.3338 |
| 6774 | 39.944 | 29.049 | 27.518 | 2.8158 |
| 7124 | 7.5393 | 7.443 | 2.8645 | 2.4081 |
| 7128 | 2.9995 | 3.0067 | 1.0856 | 1.9983 |
| 7157 | 102 | 58.463 | 88.935 | 2.9122 |
| 7422 | 10.992 | 9.8995 | 5.3072 | 2.4182 |

Part VI: Matrix of Shortest Paths Among Sinomenine-Matrine-Related Genes 4,4,4,4,3,4,5,5,3,2,4,4,4,1,4,4,4,4,3,4,3,4,4,3,4,3,3,3
1,1,3,3,3,2,4,4,2,3,4,3,3,2,3,2,4,3,3,2,3,3,1,2,1,2,2,3,0,3,2
0,1,4,4,3,3,4,4,2,3,5,4,3,3,3,3,4,3,4,3,4,4,2,3,2,3,3,4,1,3,3
2,2,3,3,3,3,3,3,2,3,4,4,2,2,3,3,3,3,4,4,2,2,2,3,3,3,1,3,2
2,1,4,2,2,3,4,4,2,3,3,3,2,2,2,3,3,2,2,2,3,3,2,2,3,2,2,2,2
3,2,4,2,2,3,4,4,3,4,5,3,3,3,3,4,5,2,2,2,4,4,2,3,3,3,2,3,2,4,3
2,1,4,2,2,2,3,3,2,3,3,3,2,2,3,2,2,2,4,3,2,2,2,2,2,2,2,2,2,2
2,2,3,3,3,3,4,4,2,3,5,3,3,3,3,3,3,3,3,3,4,2,2,2,3,3,2,3,1,3,2
3,3,4,3,3,3,4,4,2,3,5,3,3,3,3,3,4,4,5,3,3,3,3,4,3,3,3,2,3,2,4,3
3,4,3,3,2,4,2,3,5,3,4,2,4,4,5,3,3,3,3,4,3,3,3,2,3,2,4,3
1,0,4,3,3,3,4,4,2,3,4,3,3,3,3,3,4,3,3,2,3,4,2,3,2,3,2,3,1,3,3
4,3,4,4,4,4,4,4,3,3,5,2,4,3,4,4,5,2,4,4,4,3,3,3,4,3,4,4,3,4,3
3,2,3,2,2,3,3,3,1,4,4,3,3,3,3,4,4,2,2,2,3,4,2,2,3,3,2,2,2,3,2
3,2,3,3,3,3,3,3,2,3,4,3,3,3,3,4,4,3,3,3,3,3,2,3,2,2,2,2,2,3,2
3,2,4,3,3,2,4,4,2,3,5,3,4,3,4,4,4,3,3,4,4,2,3,3,3,3,3,2,3,3
3,2,3,1,1,3,4,4,2,3,4,3,3,2,3,4,4,1,1,1,3,4,2,2,3,2,1,2,2,3,2
2,3,4,3,3,4,4,1,3,4,4,3,3,3,4,4,3,3,3,4,3,3,3,2,3,2,3,2,4,3
2,3,4,4,3,2,4,4,2,3,4,4,3,3,3,3,4,4,4,3,2,3,3,3,2,2,3,3
3,2,4,3,3,3,4,4,1,3,4,2,3,3,3,4,4,3,3,3,3,4,3,3,3,2,2,3,2,3,3
2,2,4,4,4,2,4,4,3,3,4,3,3,3,3,3,4,4,4,3,4,3,2,3,0,3,2,2,1,3,3
3,2,2,2,2,3,3,3,2,3,3,3,2,2,2,3,3,2,2,2,4,3,2,1,3,3,2,2,2,3,1
2,2,3,3,3,3,2,2,2,3,4,3,2,3,2,3,3,3,3,3,4,3,2,2,3,3,2,2,2,3,2
3,2,3,2,2,3,4,4,1,2,4,3,3,1,3,4,4,2,2,2,2,3,2,3,3,1,2,3,2,3,3
3,3,1,3,3,3,5,5,3,2,4,4,3,2,3,4,4,3,4,3,4,2,2,3,3,2,2,3,2,3,3
2,1,4,3,3,2,3,3,2,2,4,3,2,2,3,4,4,2,3,3,3,3,2,3,2,2,2,2,3,2
2,2,4,3,2,3,3,3,0,3,4,3,2,3,4,4,3,3,3,3,4,2,3,3,2,3,3,2,3,3
4,4,4,4,3,5,5,5,3,4,5,4,4,4,4,5,5,4,5,4,6,5,4,4,5,4,4,5,4,4,4
3,3,3,3,2,3,4,4,2,1,4,4,3,1,3,4,4,3,4,3,4,2,3,3,3,2,3,2,3,2
3,2,4,2,2,2,4,4,2,3,4,3,3,2,3,4,3,2,2,2,4,4,2,3,3,3,2,3,2,2,3
3,3,4,3,3,3,4,4,2,3,4,3,3,2,4,4,5,3,3,3,3,4,3,2,3,2,3,2,3,2,4,2
4,3,4,3,4,5,5,4,4,5,5,4,4,2,3,5,5,5,5,6,4,4,4,4,4,3,4,4
3,3,3,3,3,3,4,4,3,3,4,3,3,3,1,3,4,4,4,4,5,3,3,3,3,3,3,3,2,3,3
3,3,3,4,3,3,5,5,3,2,4,4,3,2,4,4,3,4,4,4,5,3,3,3,3,3,4,3,2,2,3
4,4,2,3,4,4,5,5,4,2,4,3,3,2,4,3,4,2,4,4,3,3,3,4,4,2,3,4,3,3,4
2,3,3,3,3,4,4,3,2,4,4,3,2,3,3,3,3,4,4,5,3,3,3,3,2,4,3,3,2,3
4,4,3,4,4,5,5,4,4,4,4,5,4,6,4,4,4,4,4,3,4
4,2,2,2,4,4,4,4,5,5,4,4,4,5,4,4,4,6,3,3,3,4,4,3
3,3,4,4,3,3,3,3,3,3,4,4,3,3,4,3,3,4,5,3,2,3,3,3,3,3,3,3
3,3,3,1,3,3,5,5,2,2,4,3,3,2,3,4,4,2,3,3,3,2,3,2,3,0,2,3,2,3,2
3,3,3,2,3,4,4,3,2,3,4,3,1,3,3,3,2,4,2,4,3,3,3,2,2,3,2,2,2,2
3,3,4,3,3,4,4,4,3,2,5,3,3,3,2,4,3,5,3,3,3,3,4,3,3,3,3,3,2,4,3
3,3,2,2,2,3,3,3,3,3,1,2,4,2,1,2,4,4,3,4,2,4,2,2,2,2,3,2,3,2
3,3,3,3,2,3,4,4,3,2,3,4,2,2,2,4,4,3,3,3,3,4,3,3,1,3,2,3,2,2,3,0
3,3,4,4,3,3,3,4,4,3,3,3,4,0,3,2,4,4,3,4,3,5,4,3,2,3,3,3,3,3,2
3,2,3,2,2,3,4,4,3,2,4,4,3,2,3,4,4,2,2,2,3,3,2,3,2,2,0,1,2,3,3
4,3,4,2,2,4,4,4,3,4,5,4,4,3,4,5,4,2,0,2,4,4,3,3,4,3,2,3,3,4,3
2,2,3,3,2,2,3,3,2,2,3,3,1,2,1,3,3,2,3,3,4,3,2,1,2,2,2,2,2,2,1
3,3,3,3,2,3,4,4,3,2,3,3,3,2,3,3,3,4,2,3,3,3,3,3,2,3,3,2,2,2
4,3,3,3,3,3,5,5,3,2,4,4,3,1,3,4,4,3,4,2,4,3,4,3,3,2,2,3,3,3
3,3,3,2,3,5,5,3,2,4,4,2,2,3,4,3,1,3,3,4,2,3,3,3,1,2,3,2,2,3
3,3,3,3,2,3,4,4,2,1,3,3,3,0,3,3,3,3,3,2,3,2,3,3,3,2,2,3,2,2,2
3,3,3,3,2,4,4,3,2,4,3,3,2,3,3,3,2,3,3,3,4,1,2,3,2,2,2,2,2,2
3,3,4,4,3,3,4,4,3,3,3,4,2,3,0,4,4,3,4,4,5,4,3,2,3,3,3,3,3,3,2

Part VII: Matrix of Shortest Paths Among Sinomenine-Honokiol-Related Genes 1,1,3,3,3,2,4,4,2,3,4,3,3,2,3,2,4,3,3,2,3,3,1,2,1,2,2,3,0,3,2
3,2,3,2,2,3,4,4,3,2,4,4,2,2,2,3,3,2,3,3,2,2,0,1,2,3,3
4,4,4,4,4,4,6,6,4,3,5,4,4,3,4,4,5,2,4,4,4,3,4,4,4,4,4,4,3
1,1,3,3,3,3,3,2,3,4,4,3,3,3,3,4,2,3,3,3,4,2,3,2,3,2,3,1,3,3
2,1,4,3,2,3,3,2,2,4,3,2,2,3,4,4,2,3,3,3,3,2,3,2,2,2,2,3,2
2,1,4,4,4,3,4,4,3,4,5,4,4,3,3,5,4,4,3,4,4,2,3,2,3,3,4,1,4,3
4,3,3,3,3,4,4,4,3,3,4,4,2,3,4,4,3,3,3,5,4,3,2,4,2,3,3,3,3,2
0,1,4,4,3,3,4,4,2,3,5,4,3,3,3,3,4,3,4,3,4,4,2,3,2,3,3,4,1,3,3
1,0,4,3,3,3,4,4,2,3,4,3,3,3,3,3,4,3,3,2,3,4,2,3,2,3,2,3,1,3,3
6,6,7,6,5,6,6,6,5,6,6,3,5,5,5,6,7,5,6,6,7,6,5,5,5,5,6,6,5,6,5
3,3,5,5,4,4,4,4,4,5,5,5,4,4,4,4,5,4,4,5,5,3,4,3,4,4,4,2,5,4
3,2,4,3,3,3,3,3,4,4,4,3,3,3,4,3,3,3,3,4,4,2,3,3,3,3,3,2,3,3
3,3,4,2,2,3,5,5,3,5,4,3,3,3,4,4,0,2,2,4,3,3,3,4,2,2,3,3,3,3
4,4,4,4,4,4,6,6,4,4,6,4,4,4,4,5,6,4,4,4,5,4,4,4,4,4,4,5,4
2,2,4,4,4,2,4,4,3,3,4,3,3,3,3,4,4,4,3,4,3,2,3,0,3,2,2,1,3,3
3,3,3,3,2,2,3,3,2,2,4,3,3,2,2,3,3,3,3,3,4,2,2,1,2,3,3,2,2,2,1
3,3,3,3,4,4,4,3,1,3,4,3,1,3,4,3,3,3,1,4,2,3,3,3,2,3,4,2,2,3
3,2,4,3,2,4,4,3,3,4,3,3,3,4,4,3,3,3,3,4,3,2,3,2,3,3,2,3,3,3

Part VIII: Matrix of Shortest Paths Among Sinomenine-Luteolin-Related Genes 2,2,3,3,3,2,4,4,1,2,4,3,3,2,3,4,3,3,3,4,3,2,2,3,3,2,2,2,2
2,3,2,2,2,4,4,2,3,4,3,2,2,2,4,4,2,2,2,3,3,2,2,2,2,2,2,2,3,2
0,1,4,4,3,3,3,4,4,2,3,5,4,3,3,3,3,4,3,4,3,4,4,2,3,3,3,4,1,3,3

1,0,4,3,3,3,4,4,2,3,4,3,3,3,3,3,4,3,3,2,3,4,2,3,2,3,2,3,1,3,3
1,1,3,3,3,3,3,3,2,3,4,4,3,3,3,3,4,2,3,3,3,4,2,3,2,3,2,3,1,3,3
2,1,4,3,3,2,3,3,2,2,4,3,2,2,3,4,4,2,3,3,3,3,3,2,3,2,2,2,2,3,2
2,1,4,3,3,2,3,3,1,2,4,4,3,3,3,4,4,3,3,3,3,3,2,3,3,2,2,2,2,3,3
2,3,4,3,3,3,4,4,1,3,4,4,3,3,3,4,4,3,3,3,4,3,3,3,3,2,3,3,2,4,3
3,2,3,2,2,3,3,3,1,4,4,3,3,3,3,4,4,2,2,2,3,4,2,2,3,3,2,2,2,3,2
3,3,4,4,4,0,4,3,3,4,3,3,3,3,4,4,3,4,4,4,3,3,3,2,3,3,2,2,3,3
2,2,4,3,3,3,3,3,1,2,4,4,3,3,3,3,4,3,3,3,3,3,2,3,2,2,3,3,1,3,3
2,2,3,3,3,3,4,4,2,3,4,3,3,3,3,3,4,3,3,3,4,4,2,2,2,3,2,3,1,3,2
4,3,5,4,4,4,5,5,4,4,4,4,4,3,3,5,5,4,4,4,4,5,5,4,4,2,4,3,4,3,4,4
4,3,5,4,4,3,4,4,3,3,4,0,4,3,4,4,5,4,4,4,4,4,3,4,3,3,4,3,3,4,4
2,2,3,3,2,2,3,3,2,2,3,3,1,2,1,3,3,2,3,3,4,3,2,1,2,2,2,2,2,2,1
2,2,3,3,3,3,3,3,2,3,4,4,2,2,2,3,3,3,3,3,4,4,2,2,2,3,3,3,1,3,2
3,2,3,1,1,3,4,4,2,3,4,4,3,3,3,4,4,1,1,1,3,4,2,2,3,2,1,2,2,3,2
3,3,3,3,3,3,4,4,2,3,4,4,3,2,3,4,4,3,3,3,3,3,2,3,3,2,3,3,2,3,3
3,3,4,3,3,3,4,4,2,3,4,3,3,2,3,4,4,3,3,3,3,4,2,3,3,2,2,3,2,3,3
3,2,3,3,2,3,3,3,2,2,2,3,1,2,2,3,3,3,3,3,4,3,2,1,3,3,3,3,2,2,1
4,4,4,4,4,4,4,4,4,3,5,5,4,3,4,4,0,4,4,4,6,4,3,4,4,4,4,4,4,1,4
4,4,4,4,4,4,4,4,4,5,5,5,4,4,4,5,2,5,4,5,6,5,3,4,4,5,4,4,4,3,4
4,3,4,2,2,4,4,4,3,4,5,4,4,3,4,5,4,2,0,2,4,4,3,3,4,3,2,3,3,4,3
3,2,2,2,2,4,5,5,3,2,4,4,3,2,4,4,4,2,2,0,4,3,3,3,3,3,2,3,2,3,3
3,2,3,1,1,3,4,4,2,3,4,3,3,2,3,4,4,1,1,1,3,4,2,2,3,2,1,2,2,3,2
2,1,3,2,2,2,3,3,2,3,4,3,2,2,2,3,4,2,2,2,3,3,2,2,2,2,1,2,1,3,2
2,1,3,2,2,3,4,4,2,3,4,4,2,3,3,3,3,2,2,1,3,4,2,2,2,2,2,1,2,2
2,1,3,2,2,3,4,4,2,3,3,3,3,2,3,4,2,2,2,2,2,2,2,2,1,2,1,3,2
2,2,3,3,3,3,3,3,2,4,3,3,3,3,3,3,3,3,3,4,3,0,3,2,3,2,3,1,3,3
3,2,4,3,3,2,4,4,3,3,4,3,3,3,3,4,4,3,3,3,4,3,2,3,2,3,3,2,3,3
2,1,4,4,3,2,4,4,3,3,5,4,3,3,3,3,3,2,4,3,4,3,2,3,2,3,3,4,1,2,3
3,2,3,3,2,3,3,3,2,3,3,3,2,3,1,3,3,3,3,3,5,3,2,2,2,3,3,3,2,2,2
3,3,5,5,5,3,5,5,4,4,5,4,4,4,4,4,5,5,5,4,5,4,3,4,1,4,3,3,2,4,4
2,2,4,4,4,2,4,4,3,3,4,3,3,3,3,3,4,4,4,3,4,3,2,3,0,3,2,2,1,3,3
3,2,2,2,2,3,3,3,2,3,3,3,2,2,2,3,3,2,2,2,4,3,2,1,3,3,2,2,2,3,1
3,2,3,2,2,3,4,4,3,2,4,4,3,2,3,4,4,2,2,2,3,3,2,3,2,2,0,1,2,3,3
4,3,4,4,4,2,4,4,3,4,5,4,4,4,4,5,4,3,4,4,5,4,2,4,3,3,2,2,3,4,4
1,1,3,3,3,2,4,4,2,3,4,3,3,2,3,2,4,3,3,2,3,3,1,2,1,2,2,3,0,3,2
3,3,3,3,2,3,4,4,3,2,3,4,2,2,2,4,4,3,3,3,4,3,3,1,3,2,3,2,2,3,0

What is claimed is:

1. A computer implemented method for determining synergistic effect of a medicine combination including two medicines relating to a disease on the basis of a gene network and medicine-effective genes of each and/or any of said two medicines, comprising:
   determining a synergy factor ($ST_{1,2}$) of said two medicines, by a computer, on the basis of distribution of medicine-effective genes of said two medicines in said gene network;
   determining a medicine similarity factor $AS_{1,2}$ of said two medicines by a computer, on the basis of similarity between a set of symptoms which one of said two medicines relates to and set of symptoms which another of said two medicines relates to;
   determining extent of synergistic effect of said two medicines, by a computer, according to a product of said synergy factor and said similarity factor; wherein said step of determining a synergy factor ($ST_{1,2}$) of said two medicines comprises:
   for each medicine of said two medicines, determining, by a computer, a node importance factor (IP) for each gene in a subset of medicine-effective genes of said medicine;
   taking a value representing a normalized weighted average of said node importance factor (IP) over said subset as said synergy factor ($ST_{1,2}$), wherein the weight of each node importance factor (IP) of said weighted average is negatively correlated to the minimum of the shortest network paths among medicine-effective genes of said two medicines, and
   said step of determining said medicine similarity factor ($AS_{1,2}$) of said two medicines comprises:
   determining, by a computer, a symptom similarity factor ($P_{i,j}$) between a symptom which one of said two medicines relates to and a symptom which another of said two medicines relates to,
   taking a value representing an average of said symptom similarity factor ($P_{i,j}$) over a set of symptoms which at least one of said two medicines relates to as said medicine similarity factor ($AS_{1,2}$).

2. A method for determining synergistic effect as defined in claim 1, wherein said node importance factor (IP) is determined by a comprehensive processing of at least one parameter in the following parameters relating to each gene in said subset of genes:
   a parameter (NodeRank) indicating an eigenvector corresponding to the maximum eigenvalue of a network-associated matrix of said gene network,
   a parameter (Betweenness) indicating the number of shortest paths among all genes in said gene network which go through said gene, and
   a parameter (Closeness) indicating the inverse of the sum of the shortest paths from said gene to each of all other genes in the network.

3. A method for determining synergistic effect as defined in claim 2, wherein
   said parameter (NodeRank) indicating an eigenvector corresponding to the maximum eigenvalue of a network-associated matrix of said gene network indicates:

$$P(A) = \frac{1-d}{N} + d \sum_{v \in L_v} \frac{P(v)}{N_v}$$

where N is the number of all nodes in the network, d is an attenuating factor smaller than 1, which indicates uncertainty of edges in the network, $L_v$ is the set of nodes which directly connects to node A, and $N_v$ is the number of edges of node v;
said parameter (Betweenness) indicating the number of shortest paths among all nodes in said gene network which go through said gene indicates $$C_B(w) = \sum_{s \in V} \sum_{d \neq s \in V} \frac{\sigma_{sd}(w)}{\sigma_{sd}}$$

where $\sigma_{sd}$ is the number of shortest paths between any two nodes in said gene network, $\sigma_{sd}(w)$ is the number of paths among said shortest paths which go through node w, and V is the set of nodes in said network which connects to node v, and
said parameter (Closeness) indicating the inverse of the sum of the shortest paths from said gene to each of all other genes in the network indicates:

$$C(v) = \frac{1}{\sum_{t \in V} d_{v,t}}$$

where V is the set of nodes in said network which connects to node v, $d_{v,t}$ is the shortest path from node v to node t, wherein said synergy factor ($ST_{1,2}$) of said two medicines is determined as:

$$ST_{1,2} = \frac{1}{2} \times \left( \frac{\sum_i IP_1(i) \times \exp(-\min(d_{i,j}))}{\sum_i IP_1(i)} + \frac{\sum_j IP_2(j) \times \exp(-\min(d_{j,i}))}{\sum_j IP_2(j)} \right)$$ Formula (1)

where:
- $IP_1(i)$ and $IP_1(j)$ are said factors of node importance of network nodes i and j respectively,
- $d_{i,j}$ is the shortest network path from node i to node j, and $d_{j,i}$ is the shortest network path from node j to node i, and wherein said medicine similarity factor ($AS_{1,2}$) is determined as $$AS_{1,2} = \frac{\sum_{i,j} P_{i,j}}{N},$$

where:
Pi,j is the similarity factor between disease i in a first group of diseases which one of said two medicines corresponds to and disease j in a second group of diseases which another of said two medicines corresponds to, and N is for all pairs of diseases between said first group of diseases and said second group of diseases.

4. A method for determining synergistic effect as defined in claim 2, wherein said comprehensive processing comprises principal components analysis (PCA).

5. A method for determining synergistic effect as defined in claim 4, wherein said gene network can be anyone of:
- a network constructed by all network relations in HPRD Database,
- a network constructed by all network relations in KEGG Database, or
- a disease-related gene network constructed by known disease-related genes of said disease.

6. A method for determining synergistic effect as defined in claim 5, further comprising:
constructing a disease-related gene network of said disease, comprising:
- based on known disease-related genes of said disease, for each pair/group of genes in KEGG and HPRD Databases, determining whether all genes in said pair/group appear in said known disease-related genes of said disease, and
- when all genes in said pair/group appear in said known disease-related genes of said disease, determining that the genes in said pair/group are adjacent genes in said disease-related gene network.

7. A method for determining synergistic effect as defined in claim 5, wherein the shortest paths among medicine-effective genes of said two medicines are determined by using the Floyd Algorithm.

8. A method for determining synergistic effect as defined in claim 1, wherein said gene network can be any one of:
- a network constructed by all network relations in Human Protein Reference Database (HPRD Database),
- a network constructed by all network relations existed in already published Kyoto Encyclopedia of Genes and Genomes (KEGG Database), or
- a disease-related gene network constructed by known disease-related genes of said disease.

9. A method for determining synergistic effect as defined in claim 1, further comprising:
constructing a disease-related gene network of said disease, comprising:
- based on known disease-related genes of said disease, for each pair/group of genes in KEGG and HPRD Databases, determining whether all genes in said pair/group of genes are included in said known disease-related genes of said disease, and
- when all genes in said pair/group appear in said known disease-related genes of said disease, determining that the genes in said pair/group of genes are adjacent genes in said disease-related gene network,
- and, using said disease-related gene network of said disease as said gene network.

* * * * *

UNITED STATES PATENT AND TRADEMARK OFFICE
CERTIFICATE OF CORRECTION

PATENT NO.       : 8,112,230 B2  
APPLICATION NO.  : 12/436844  
DATED            : February 7, 2012  
INVENTOR(S)      : :Li et al.

Page 1 of 1

It is certified that error appears in the above-identified patent and that said Letters Patent is hereby corrected as shown below:

Just below UNITED STATES PATENT (12) at the top left of the cover page, please change the first-named inventor as follows in parenthesis:

"Li et al."

Just below the title of the invention (54) on the first page, please change the order of inventors at (75) to read as follows in parenthesis:

"Inventors: Shao Li, Beijing, (CN); Ningbo Zhang, Beijing, (CN); Bo Zhang, Beijing (CN)"

Signed and Sealed this  
Twenty-ninth Day of May, 2012

David J. Kappos  
*Director of the United States Patent and Trademark Office*